(12) United States Patent
Verhoeven et al.

(10) Patent No.: US 9,616,207 B2
(45) Date of Patent: Apr. 11, 2017

(54) TREATMENT OF THE EAR

(71) Applicant: Cochlear Limited, Macquarie University, NSW (AU)

(72) Inventors: Kristien Johanna Maria Verhoeven, Mechelen (BE); Daniel Smyth, Mechelen (BE); Jonathon Kirk, Centennial, CO (US); Claudiu G. Treaba, Jericho, NY (US); Marcus Andersson, Gothenburg (SE)

(73) Assignee: Cochlear Limited, Macquarie University, NSW (AU)

( * ) Notice: Subject to any disclaimer, the term of this patent is extended or adjusted under 35 U.S.C. 154(b) by 161 days.

(21) Appl. No.: 14/315,825

(22) Filed: Jun. 26, 2014

(65) Prior Publication Data
US 2015/0374964 A1 Dec. 31, 2015

(51) Int. Cl.
*A61M 31/00* (2006.01)
*A61M 5/142* (2006.01)
*A61F 11/00* (2006.01)
*A61M 5/145* (2006.01)
*A61M 5/148* (2006.01)

(52) U.S. Cl.
CPC ........... *A61M 31/002* (2013.01); *A61F 11/00* (2013.01); *A61M 5/1428* (2013.01); *A61M 5/14276* (2013.01); *A61M 5/145* (2013.01); *A61M 5/148* (2013.01); *A61M 2205/075* (2013.01); *A61M 2210/0662* (2013.01); *A61M 2210/0668* (2013.01); *A61M 2210/0687* (2013.01); *H04R 2225/67* (2013.01)

(58) Field of Classification Search
CPC ............ A61M 31/002; A61M 5/14276; A61M 5/14224; A61M 2210/0662; A61M 2210/0668; A61M 2205/8287; A61M 5/1428; A61F 11/00; A61F 11/02
See application file for complete search history.

(56) References Cited

U.S. PATENT DOCUMENTS

| | | | |
|---|---|---|---|
| 3,731,681 A * | 5/1973 | Blackshear | A61M 5/141 222/386.5 |
| 3,951,147 A | 4/1976 | Tucker et al. | |
| 4,013,074 A | 3/1977 | Siposs | |
| 4,487,603 A | 12/1984 | Harris | |
| 4,540,400 A | 9/1985 | Hooven | |
| 4,544,371 A * | 10/1985 | Dormandy, Jr. | A61M 5/1428 604/185 |
| 4,548,607 A * | 10/1985 | Harris | A61M 5/1428 604/153 |
| 4,576,556 A | 3/1986 | Thompson | |
| 4,588,394 A * | 5/1986 | Schulte | A61M 5/1428 604/185 |

(Continued)

OTHER PUBLICATIONS

International Search Report and Written Opinion in International Application No. PCT/IB2015/053691, mailed Sep. 17, 2015, 15 pages.

(Continued)

*Primary Examiner* — Andrew Gilbert
(74) *Attorney, Agent, or Firm* — Edell, Shapiro & Finnan, LLC

(57) ABSTRACT

Presented herein are implantable systems and methods for long-term delivery of treatment substance to the ear of a recipient of an implantable auditory prosthesis.

12 Claims, 20 Drawing Sheets

(56) References Cited

U.S. PATENT DOCUMENTS

| | | | | |
|---|---|---|---|---|
| 4,668,231 A * | 5/1987 | de Vries | A61M 5/1428 604/153 |
| 4,673,391 A * | 6/1987 | Kondo | A61M 5/14276 128/DIG. 12 |
| 4,681,560 A * | 7/1987 | Schulte | A61M 5/1428 604/8 |
| 4,692,147 A | 9/1987 | Duggan | |
| 4,718,893 A | 1/1988 | Dorman et al. | |
| 4,813,951 A | 3/1989 | Cannon | |
| 4,883,467 A | 11/1989 | Franetzki et al. | |
| 5,045,064 A | 9/1991 | Idriss | |
| 5,088,983 A | 2/1992 | Burke | |
| 5,895,372 A | 4/1999 | Zenner et al. | |
| 6,283,944 B1 | 9/2001 | McMullen et al. | |
| 6,685,697 B1 * | 2/2004 | Arenberg | A61F 11/00 604/11 |
| 6,974,445 B2 | 12/2005 | Stergiopulos | |
| 7,044,942 B2 | 5/2006 | Jolly et al. | |
| 7,104,767 B2 * | 9/2006 | Lee | A61M 5/14276 417/413.1 |
| 7,206,639 B2 * | 4/2007 | Jacobsen | A61F 11/00 607/57 |
| 7,351,239 B2 | 4/2008 | Gill | |
| 7,569,049 B1 * | 8/2009 | Blischak | A61M 5/14276 251/129.01 |
| 7,815,615 B2 | 10/2010 | Jolly et al. | |
| 7,867,193 B2 | 1/2011 | McKenna et al. | |
| 8,080,002 B2 | 12/2011 | Stergiopulos et al. | |
| 8,211,060 B2 | 7/2012 | Steinbach | |
| 8,267,905 B2 * | 9/2012 | Lobl | A61M 5/14276 604/288.01 |
| 8,401,674 B2 * | 3/2013 | Gibson | A61M 31/002 604/256 |
| 8,712,517 B2 | 4/2014 | Jolly | |
| 9,114,230 B2 * | 8/2015 | Wilson | A61M 27/006 |
| 2002/0022793 A1 * | 2/2002 | Bertrand | A61M 27/006 604/9 |
| 2002/0087147 A1 | 7/2002 | Hooper et al. | |
| 2002/0161354 A1 | 10/2002 | Christiansen et al. | |
| 2003/0229366 A1 * | 12/2003 | Reggie | A61B 1/3137 606/158 |
| 2004/0044332 A1 | 3/2004 | Stergiopulos | |
| 2004/0064110 A1 * | 4/2004 | Forsell | A61M 5/1428 604/288.01 |
| 2004/0249365 A1 | 12/2004 | Harper et al. | |
| 2005/0182385 A1 * | 8/2005 | Epley | A61F 11/00 604/514 |
| 2005/0238506 A1 * | 10/2005 | Mescher | A61M 5/14276 417/413.1 |
| 2006/0184143 A1 * | 8/2006 | Jolly | A61M 5/14276 604/288.02 |
| 2006/0253087 A1 | 11/2006 | Vlodaver et al. | |
| 2006/0264897 A1 * | 11/2006 | Lobl | A61M 39/0208 604/506 |
| 2007/0005044 A1 | 1/2007 | Steinbach et al. | |
| 2007/0088335 A1 | 4/2007 | Jolly | |
| 2007/0213799 A1 | 9/2007 | Jolly et al. | |
| 2008/0009836 A1 * | 1/2008 | Fiering | A61F 11/002 604/891.1 |
| 2008/0053457 A1 * | 3/2008 | McDonald | A61M 16/06 128/207.17 |
| 2009/0137899 A1 * | 5/2009 | Bengtson | A61M 39/0208 600/424 |
| 2009/0209945 A1 * | 8/2009 | Lobl | A61M 5/14224 604/891.1 |
| 2011/0208161 A1 * | 8/2011 | Ivri | A61F 11/00 604/514 |
| 2012/0046595 A1 * | 2/2012 | Wilson | A61M 27/006 604/9 |
| 2013/0053823 A1 * | 2/2013 | Fiering | A61M 5/14276 604/514 |
| 2013/0181538 A1 * | 7/2013 | Calasso | A61M 5/1413 307/104 |
| 2014/0094735 A1 * | 4/2014 | Wilson | A61M 27/006 604/9 |
| 2014/0371727 A1 * | 12/2014 | Choy | A61M 5/1452 604/891.1 |

OTHER PUBLICATIONS

FDA, "PMA P080012: FDA Summary of Safety and Effectiveness Data," retrieved from http://www.accessdata.fda.gov/cdrh_docs/pdf8/P080012b.pdf, on Jun. 26, 2014, pp. 1-26.

Medtronic, "IsoMed® Implantable Constant-Flow Infusion Pump," Technical Manual, retrieved from www.medtronic.com, on Jun. 26, 2014, 70 pages.

Laser, et al., "A review of micropumps," Journal of Micromechanics and Microengineering, 14 (2004), Apr. 2004, pp. R35-R64.

Medtronic, "Synchromed® EL Programmable pumps," Implant manual, retrieved from www.medtronic.com, on Jun. 26, 2014, 40 pages.

Medtronic, "Synchromed® II Programmable pumps," Implant manual, retrieved from www.medtronic.com, on Jun. 26, 2014, 26 pages.

Durect, "Duros® Technology Platform," fact sheet, retrieved from http://www.durect.com/pdf/duros_fact_sheet2001.pdf, on Jun. 26, 2014, 2 pages.

Codman, "Codman 3000, Implantable Constant-Flow Infusion Pump," Patient Information booklet for pain Management Therapy, http://www.codmanpumps.com/PDFs/Patient_pain_booklet.pdf, Sep. 2003, 20 pages.

* cited by examiner

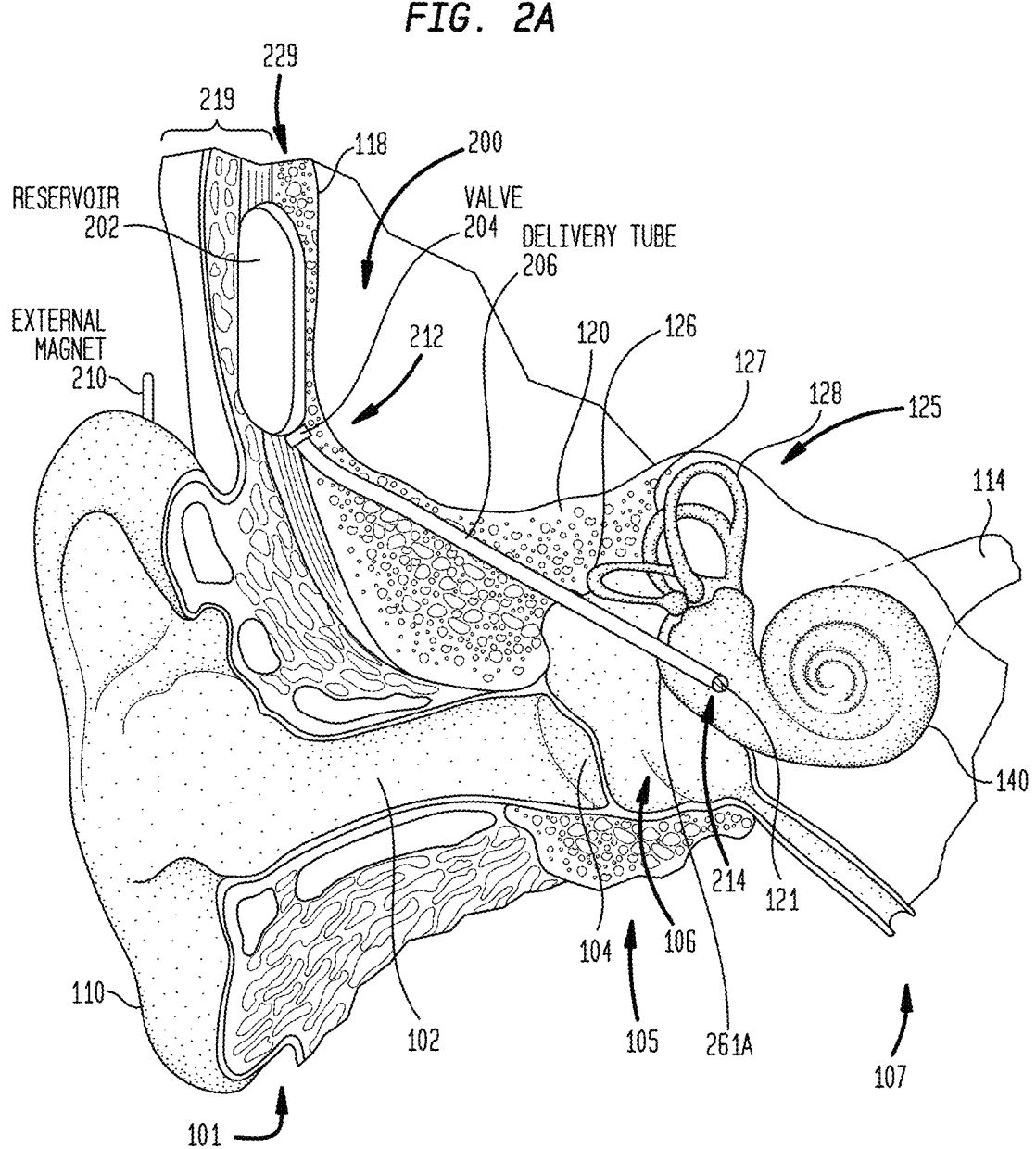

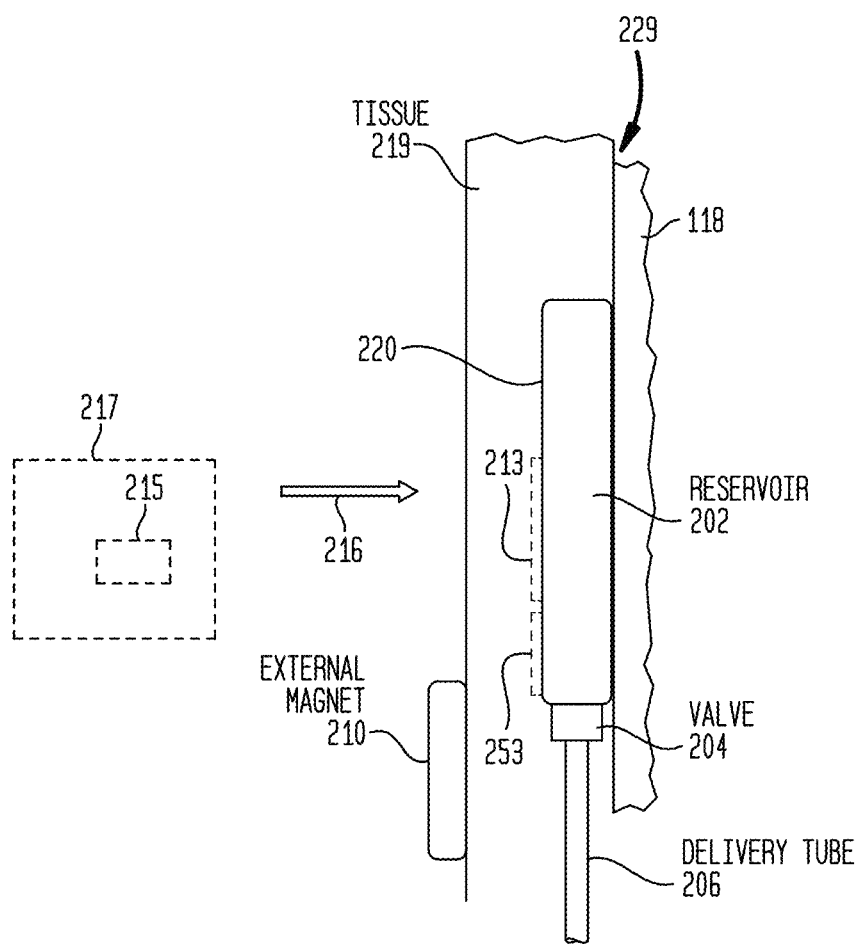

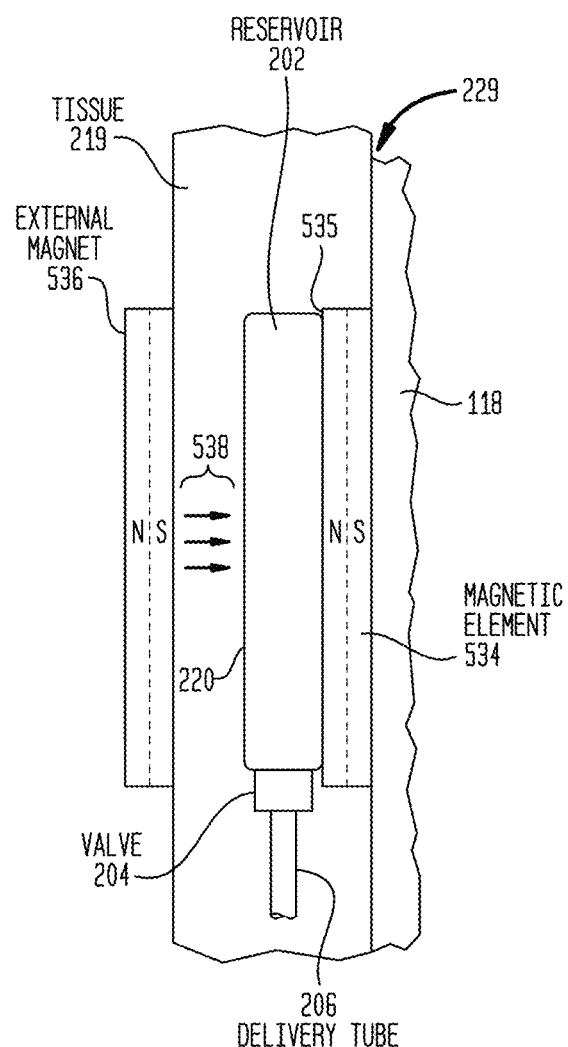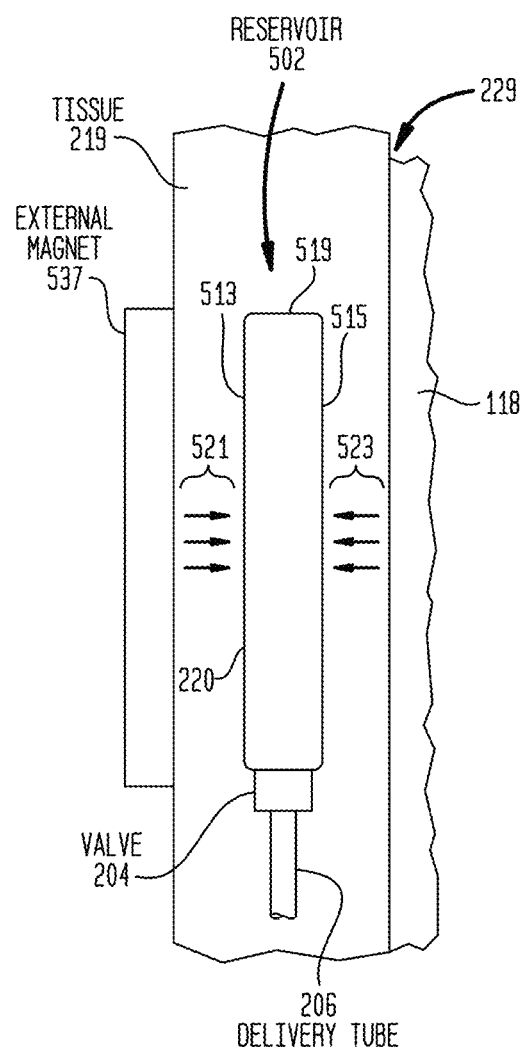

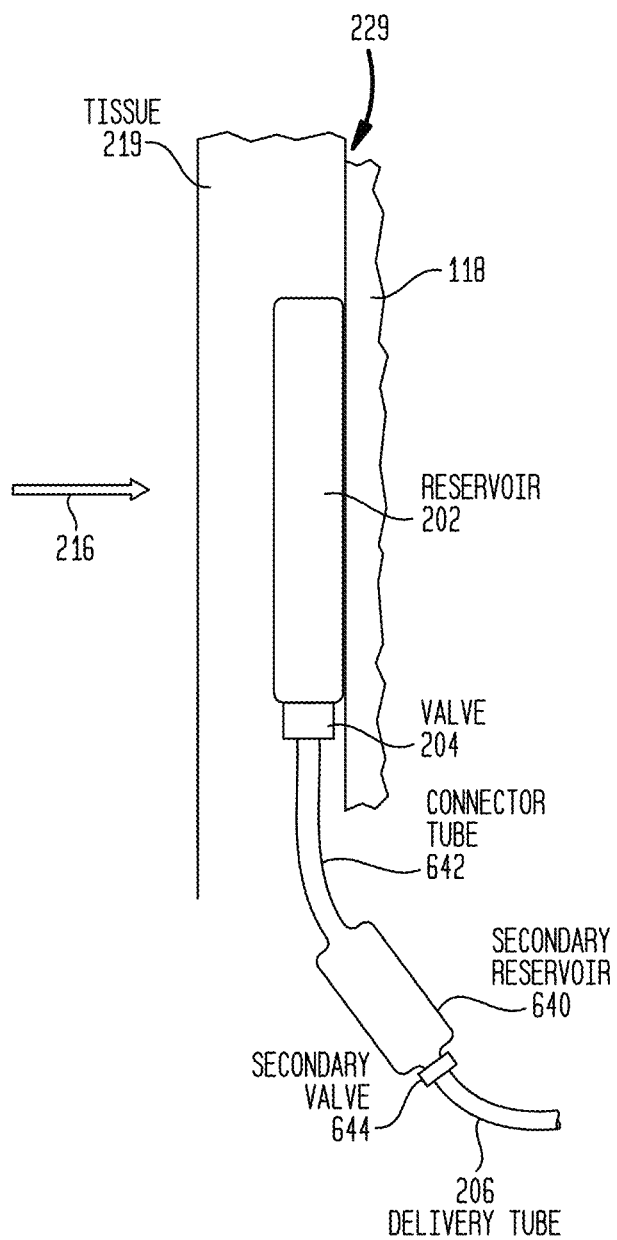

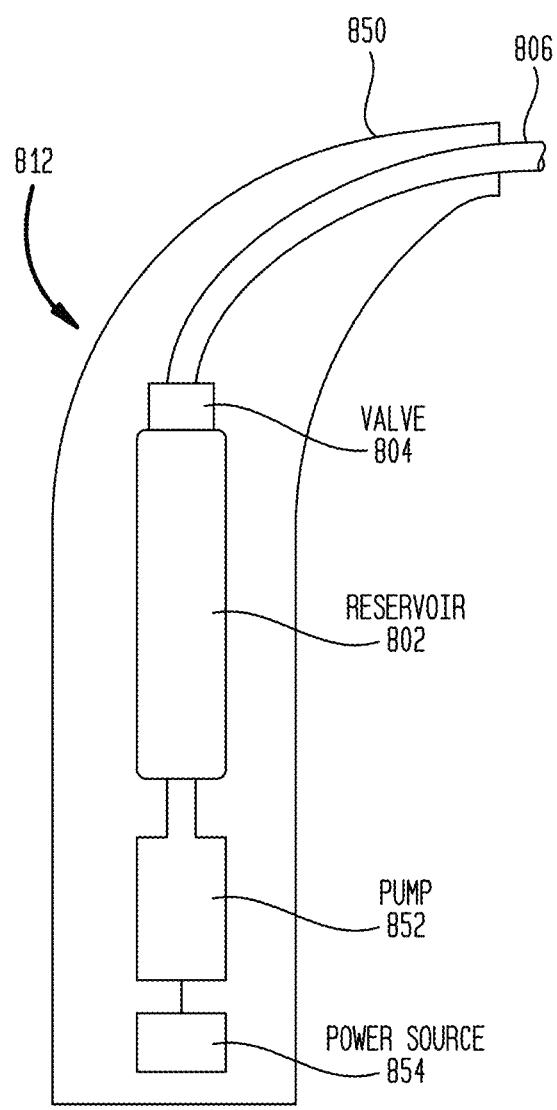

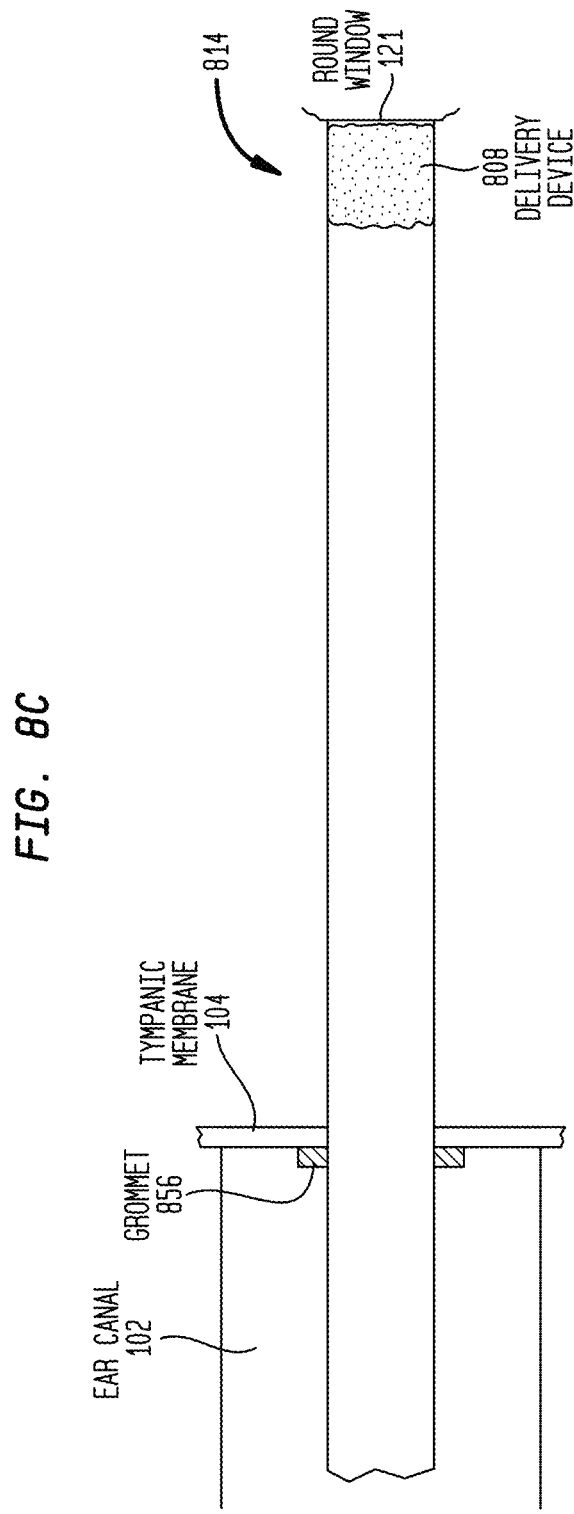

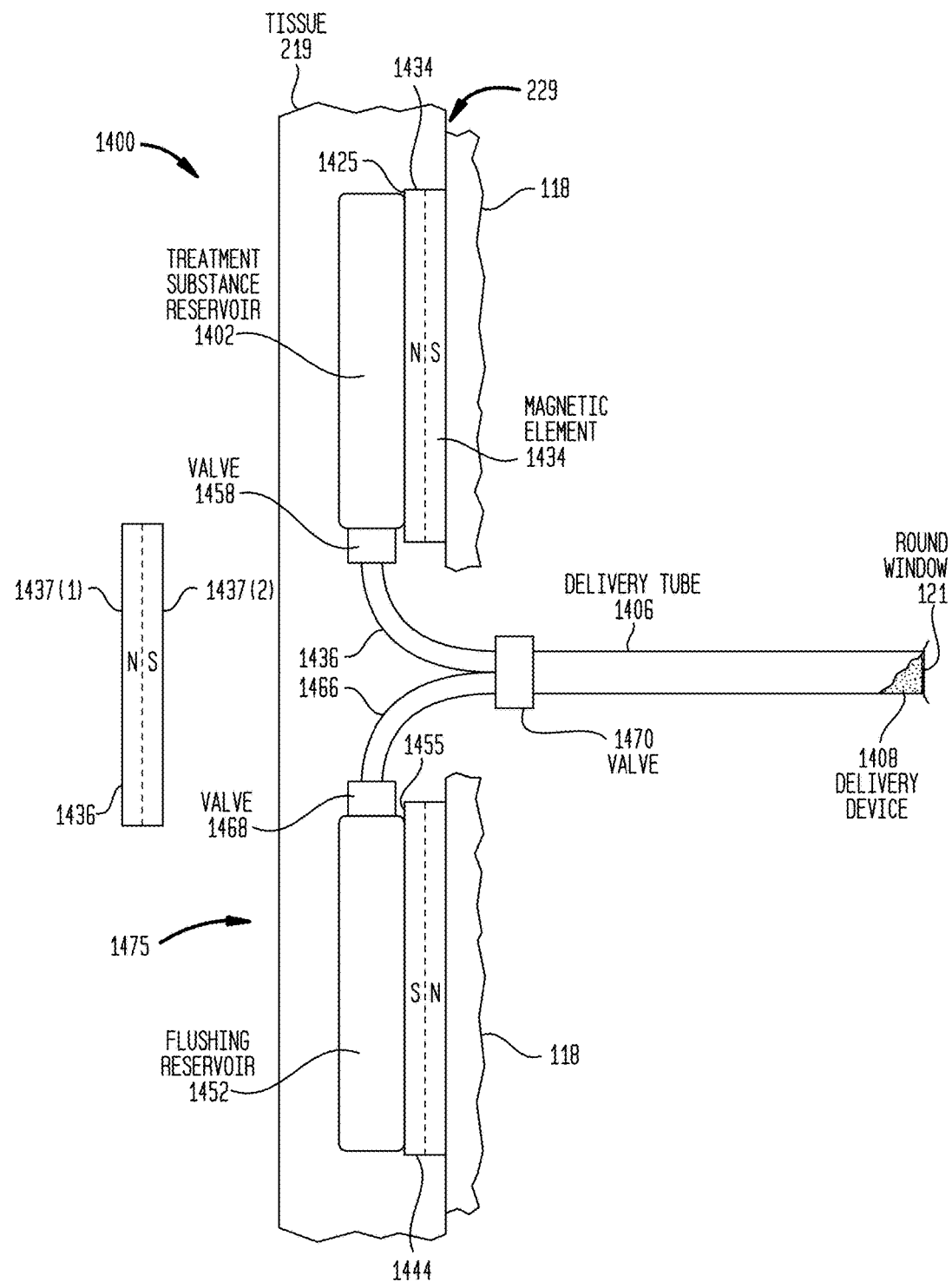

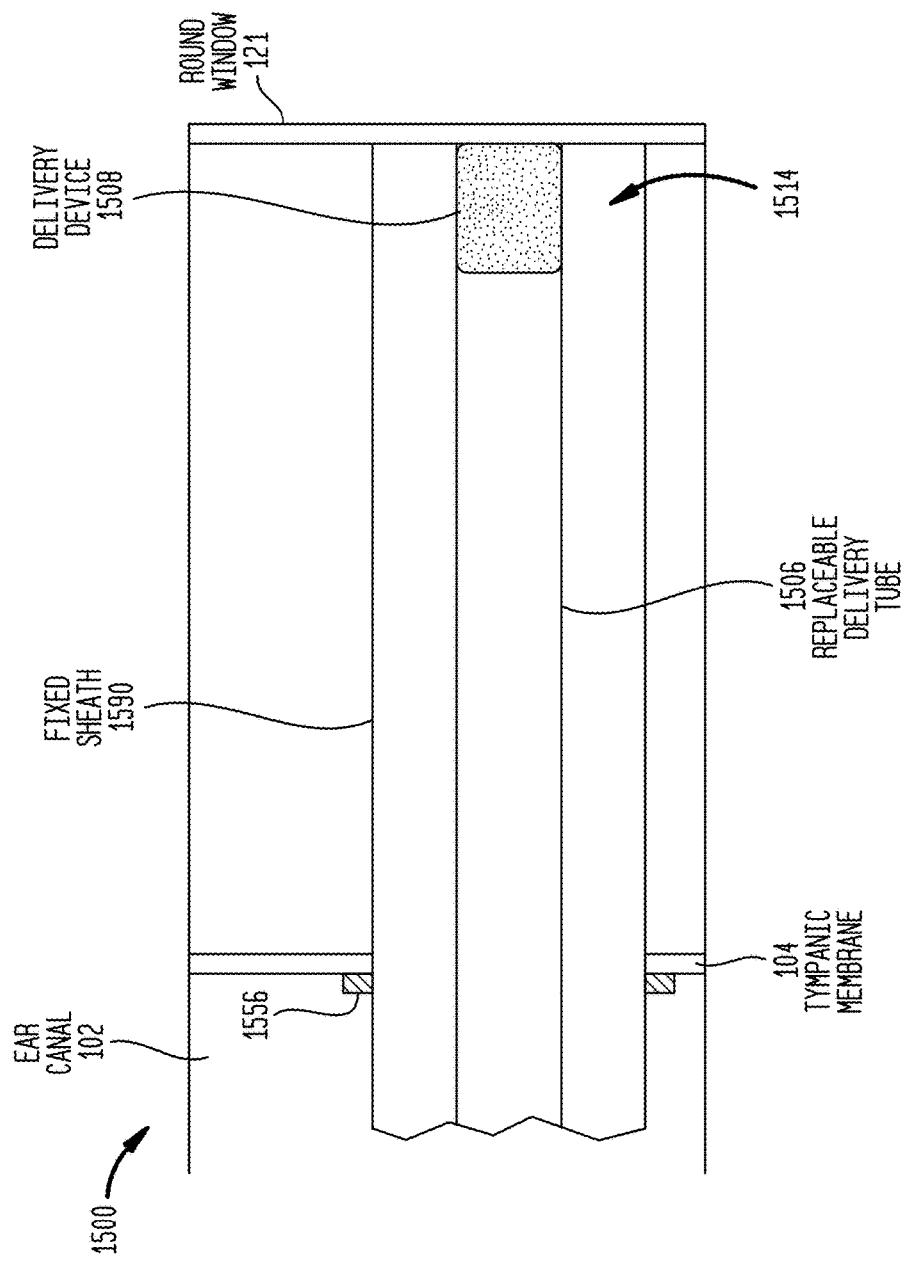

US 9,616,207 B2

TREATMENT OF THE EAR

BACKGROUND

Field of the Invention

The present invention relates generally to delivery of treatment substances to the ear of an implantable auditory prosthesis recipient.

Related Art

Individuals suffer from a variety of hearing problems, such as tinnitus, Ménière's disease, vertigo, hearing loss, etc. Hearing loss, for example, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like).

SUMMARY

In one aspect, an apparatus is provided. The apparatus comprises an implantable reservoir configured to have a treatment substance disposed therein, an implantable delivery tube having a proximal end fluidically coupled to the reservoir and a distal end positioned adjacent a target location within a recipient, and a passive activation mechanism configured to transfer a portion of the treatment substance in the reservoir to the delivery tube for delivery to the target location.

In another aspect, an apparatus is provided. The apparatus comprises an at least partially implantable elongate delivery tube configured to have a treatment substance disposed therein, wherein the delivery tube is configured to be positioned in a recipient's ear canal and pass through an opening in the recipient's tympanic membrane such that a distal end of the delivery tube is adjacent a target location within the recipient, and a delivery device disposed at the distal end of the delivery tube configured to transfer the treatment substance in the delivery tube to the target location.

BRIEF DESCRIPTION OF THE DRAWINGS

Embodiments of the present invention are described herein in conjunction with the accompanying drawings, in which:

FIG. 2A illustrates a delivery system in accordance with embodiments presented herein implanted in a recipient;

FIG. 2B illustrates a first portion of the delivery system of FIG. 2A;

FIG. 5A illustrates a delivery system in accordance with embodiments presented herein that utilizes an external magnet to force a treatment substance from a reservoir;

FIG. 5B illustrates another delivery system in accordance with embodiments presented herein that utilizes an external magnet to force a treatment substance from a reservoir;

FIG. 6 illustrates another delivery system in accordance with embodiments presented herein;

FIG. 8B illustrates a first portion of the delivery system of FIG. 8A;

FIG. 8C illustrates another portion of the delivery system of FIG. 8A;

FIG. 14 is a schematic diagram illustrating another delivery system in accordance with embodiments presented herein; and FIG. 15 is a schematic diagram illustrating a further delivery system in accordance with embodiments presented herein.

DETAILED DESCRIPTION

Presented herein are implantable systems and methods for long-term delivery of substances (e.g., biological or bioactive), chemicals, pharmaceutical agents, nanoparticles, ions, drugs, etc. (generally and collectively referred to herein as "treatment substance") to a target location within a recipient of a treatment substance delivery system and/or implantable auditory (hearing) prosthesis (e.g., bone conduction device, direct acoustic stimulator, cochlear implant, etc.). The target location may be, for example, the recipient's middle ear, inner ear, vestibular system, round window, oval window, cochleostomy, etc. Before describing illustrative embodiments of the treatment substance delivery systems and methods presented herein, a brief description of the human anatomy of a recipient's ear is first provided with reference to FIG. 1.

Figure 1:
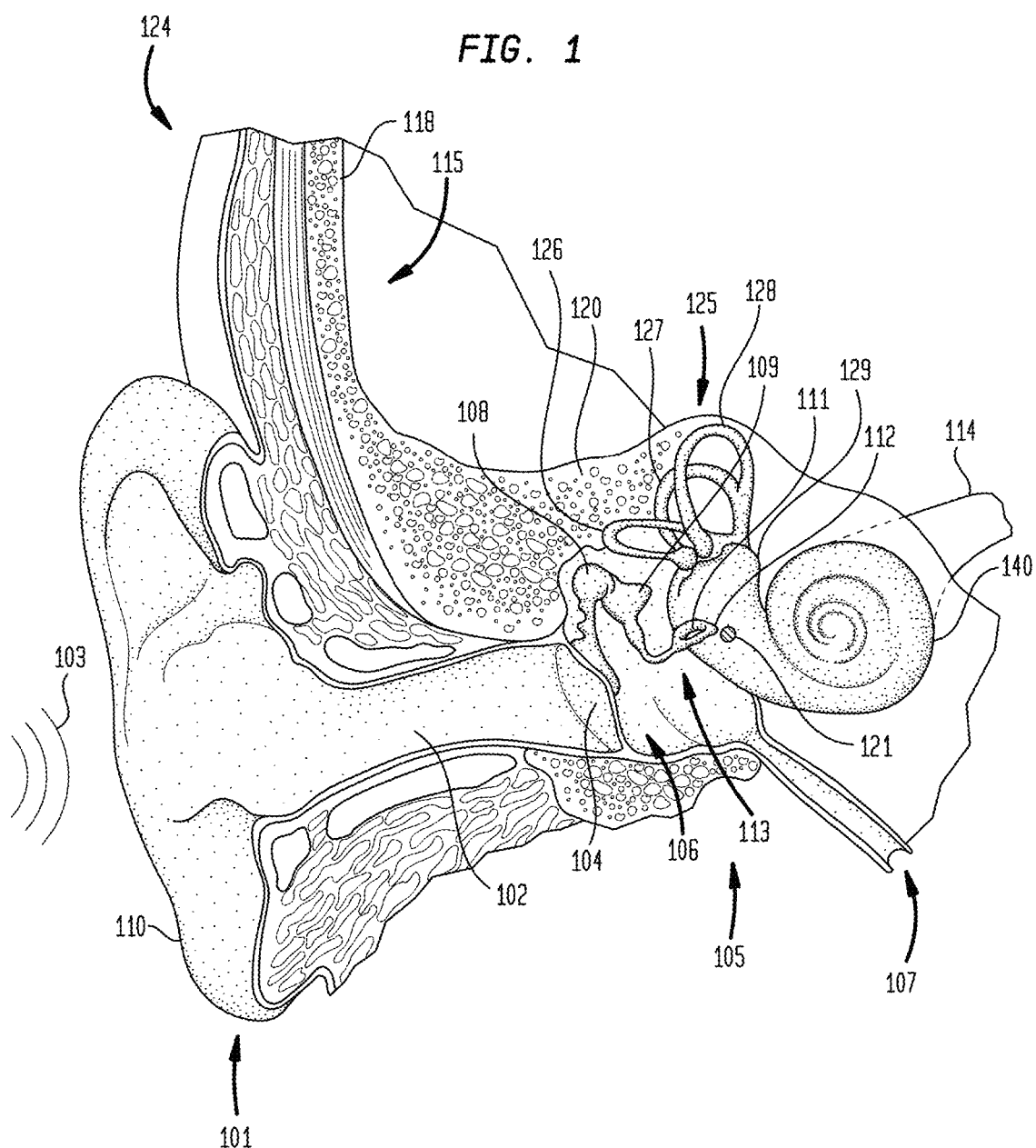
FIG. 1 is a schematic diagram illustrating the anatomy of a recipient at a location in which a delivery system herein may be implanted.

As shown in FIG. 1, a recipient's ear comprises an outer ear 101, a middle ear 105 and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121, through the bones of the middle ear 105. The bones of the middle ear 105 comprise the malleus 108, the incus 109 and the stapes 111, collectively referred to as the ossicles 106. The ossicles 106 are positioned in the middle ear cavity 113 and serve to filter and amplify the sound wave 103, causing oval window 112 to articulate (vibrate) in response to the vibration of tympanic membrane 104. This vibration of the oval window 112 sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound The human skull is formed from a number of different bones that support various anatomical features. Illustrated in FIG. 1 is the temporal bone 115 which is situated at the side and base of the recipient's skull 124. For ease of reference, the temporal bone 115 is referred to herein as having a superior portion 118 and a mastoid portion 120. The superior portion 118 comprises the section of the temporal bone 115 that extends superior to the auricle 110. That is, the superior portion 118 is the section of the temporal bone 115 that forms the side surface of the skull. The mastoid portion 120, referred to herein simply as the mastoid 120, is positioned inferior to the superior portion 118. The mastoid 120 is the section of the temporal bone 115 that surrounds the middle ear 105.

As shown in FIG. 1, semicircular canals 125 are three half-circular, interconnected tubes located adjacent cochlea 140. Vestibule 129 provides fluid communication between semicircular canals 125 and cochlea 140. The three canals are the horizontal semicircular canal 126, the posterior semicircular canal 127, and the superior semicircular canal 128. The canals 126, 127 and 128 are aligned approximately orthogonally to one another. Specifically, horizontal canal 126 is aligned roughly horizontally in the head, while the superior 128 and posterior canals 127 are aligned roughly at a 45 degree angle to a vertical through the center of the individual's head.

Each canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

It may be advantageous to have an extended delivery solution for use in the delivery of treatment substances to a target location of a recipient. In general, extended treatment substance delivery refers to the delivery of treatment substances over a period of time (e.g., continuously, periodically, etc). The extended delivery may be activated during or after surgery and can be extended as long as is needed. The period of time may not immediately follow the initial implantation of the auditory prosthesis. As such, embodiments of the present invention are directed to different features that facilitate extended delivery of treatment substances. More specifically, certain embodiments are directed to passive actuation (drive) mechanisms that eliminate the need for an implanted active (i.e., powered) pump and power source to deliver treatment substances to a target location. Additional embodiments are directed to optional fixation mechanisms that retain various components of a delivery system at a selected implanted location. Further embodiments are directed to accretion prevention (anti-accretion) mechanisms that prevent the buildup of undelivered particles within the system that can inhibit subsequent delivery of treatment substances.

Figure 2C:
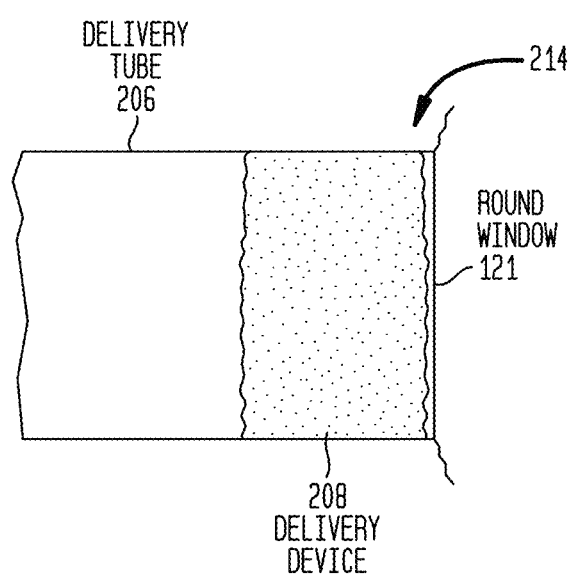
FIG. 2C illustrates a cross-sectional view of a second portion of the delivery system of FIG. 2A.

FIG. 2A illustrates an implantable delivery system 200 having a passive actuation mechanism in accordance with embodiments presented herein. The delivery system 200 is sometimes referred to herein as an inner ear delivery system because it is configured to deliver treatment substances to the recipient's inner ear (e.g., the target location is the interior of the recipient's cochlea 140). FIG. 2B illustrates a first portion of the delivery system 200, while FIG. 2C is a cross-sectional view of a second portion of the delivery system 200.

Delivery system 200 of FIGS. 2A-2C comprises a reservoir 202, a valve 204, a delivery tube 206, and a delivery device 208 (FIG. 2C). The delivery system 200 may include, or operate with, an external magnet 210. For ease of illustration, the delivery system 200 is shown separate from any implantable auditory prostheses. However, it is to be appreciated that the delivery system 200 could be used with, for example, cochlear implants, direct acoustic stimulators, bone conduction devices, etc. In such embodiments, the implantable components (e.g., reservoir, valve, delivery tube, etc.) of delivery system 200 could be separate from or integrated with the other components of the implantable auditory prosthesis.

In the embodiment of FIGS. 2A-2C, the reservoir 202 is positioned within the recipient underneath a portion of the recipient's skin/muscle/fat, collectively referred to herein as tissue 219. The reservoir 202 may be positioned between layers of the recipient's tissue 219 or may be adjacent to a subcutaneous outer surface 229 of the recipient's skull. For example, the reservoir 202 may be positioned in a surgically created pocket at the outer surface 229 (i.e., adjacent to a superior portion 118 of the temporal bone 115).

The reservoir 202 is, prior to or after implantation, at least partially filled with a treatment substance for delivery to the inner ear 107 of the recipient. The treatment substance may be, for example, in a liquid form, a gel form, and/or comprise nanoparticles or pellets. In certain arrangements, the treatment substance may initially be in a crystalline/solid form that is subsequently dissolved. For example, a reservoir could include two chambers, one that comprises a fluid (e.g., artificial perilymph or saline) and one that comprises the crystalline/solid treatment substance. The fluid may be mixed with the crystalline/solid treatment substance to form a fluid or gel treatment substance that may be subsequently delivered to the recipient.

In certain embodiments, the reservoir 202 includes a needle port (not shown) so that the reservoir 202 can be refilled via a needle injection through the skin. In other embodiments, the reservoir 202 may be explanted and replaced with another reservoir that is, prior to or after implantation, at least partially filled with a treatment substance. In accordance with certain embodiments, the reservoir 202 may have a preformed shape and the reservoir is implanted in this shape. In other embodiments, the reservoir 202 may have a first shape that facilitates implantation and a second shape for use in delivering treatment substances to the recipient. For example, the reservoir 202 may have a rolled or substantially flat initial shape that facilitates implantation. The reservoir 202 may then be configured to expand after implantation. Such embodiments may be used, for example, to insert the reservoir through a tympanostomy into the middle ear or ear canal, through an opening in the inner ear, or to facilitate other minimally invasive insertions.

The delivery tube 206 includes a proximal end 212 and a distal end 214. The proximal end 212 of the delivery tube 206 is fluidically coupled to the reservoir 202 via the valve 204. As shown in FIG. 2C, the distal end 214 of the delivery tube 206 is fluidically coupled to the recipient's round window 121. A delivery device 208 disposed within the distal end 214 of the delivery tube 206 is positioned abutting the round window 121. As described further below, the delivery tube 206 may be secured within the recipient so that the distal end 214 remains located adjacent to the round window 121.

FIGS. 2A-2C illustrate embodiments that utilize a passive actuation mechanism to produce a pumping action to transfer a treatment substance from the reservoir 202 to the delivery device 208 at the distal end 214 of the delivery tube 206. More specifically, in these illustrative embodiments, the reservoir 202 is compressible in response to an external force 216. That is, at least one part or portion of the reservoir 202, such as wall 220 or a portion thereof, is formed from a resiliently flexible material that is configured to deform in response to application of the external force 216. In certain embodiments, the positioning of the reservoir 202 adjacent the superior portion 118 of the mastoid 115 provides a rigid surface that counters the external force 216. As a result, a pressure change occurs in the reservoir 202 so as to propel (push) a portion of the treatment substance out of the reservoir through valve 204.

FIGS. 2A and 2B illustrate a specific arrangement in which the reservoir 202 includes a resiliently flexible wall 220. It is to be appreciated that the reservoir 202 may be formed from various resiliently flexible parts and rigid parts. It is also to be appreciated that the reservoir 202 may have a variety of shapes and sizes (e.g., cylindrical, square, rectangular, etc.) or other configurations. For example, in one embodiment the reservoir 202 could further include a spring mounted base that maintains a pressure in the reservoir 202 until the reservoir is substantially empty. Other mechanisms for maintaining a pressure in the reservoir may be used in other arrangements.

In certain embodiments, the external force 216 is applied manually using, for example, a user's finger. The user (e.g., recipient, clinician, caregiver, etc.) may press on the tissue 219 adjacent to the reservoir 202 to create the external force 216. In certain embodiments, a single finger press may be sufficient to propel the treatment substance through valve 204. In other embodiments, multiple finger presses may be used to create a pumping action that propels the treatment substance from the reservoir 202.

In other embodiments, the external force 216 is applied through a semi-manual method that uses an external actuator 217 (FIG. 2B). That is, the external actuator 217 may be pressed onto the soft tissue 219 under which the reservoir 202 is located. The movement (e.g., oscillation/vibration) of the actuator 217 deforms the reservoir 202 to create the pumping action that propels the treatment substance out of the reservoir.

In certain embodiments, internal and/or external magnets and/or magnetic materials may be used in the arrangements of FIGS. 2A and 2B to ensure that the actuator 217 applies force at an optimal location of the reservoir 202. For example, the reservoir 202 may include a magnetic positioning member 213 located at or near an optimal location for application of an external force from the actuator 217. The actuator 217 may include a magnet 215 configured to magnetically mate with the magnetic positioning member 213. As such, when actuator 217 is properly positioned, the magnet 215 will mate with the magnetic positioning member 213 and the force from the actuator 217 will be applied at the optimal location.

In other embodiments, a remote control, remotely placed actuator (subcutaneous or otherwise) may be alternatively used. For example, in a further arrangement, the implant includes implanted electronics 253 (shown using dotted lines in FIG. 2B). These implanted electronics 253 may be configured to, for example, control the valve 204 and/or include an actuation mechanism that can force treatment substance from the reservoir 202. In certain embodiments, the implanted electronics 253 may be powered and/or controlled through a transcutaneous link (e.g., RF link). As such, the implanted electronics 253 may include or be electrically connected to an RF coil, receiver/transceiver unit, etc.

In accordance with certain embodiments, the implanted electronics 253 may include or be connected to a sensor that is used, at least in part, to assist in control of delivery of the treatment substance to the recipient. For example, a sensor (e.g., a temperature sensor, a sensor to detect infection or bacteria growth, etc.) may provide indications of when a treatment substance should be delivered and/or when delivery should be ceased for a period of time. A sensor may also be configured to determine an impact of the treatment substance on the recipient (e.g., evaluate effectiveness of the treatment substance).

As noted, the treatment substance is released from the reservoir 202 through the valve 204. The valve 204 may be a check valve (one-way valve) that allows the treatment substance to pass there through in one direction only. This assures that released treatment substances do not back-flow into the reservoir 202. In certain embodiments, the valve 204 is a valve that is configured to open in response to the pressure change in the reservoir 202 (e.g., a ball check valve, diaphragm check valve, swing check valve or tilting disc check valve, etc.). The valve 204 may be a stop-check valve that includes an override control to stop flow regardless of flow direction or pressure. That is, in addition to closing in response to backflow or insufficient forward pressure (as in a normal check valve), a stop-check value can also be deliberately opened or shut by an external mechanism, thereby preventing any flow regardless of forward pressure. The valve 204 may be a stop-check value that is controlled by an external electric or magnetic field generated by, for example, the external magnet 210, an electromagnet, etc. In the embodiments, of FIGS. 2A and 2B, the valve is responsive to a magnetic field generated by external magnet 210. As such, the valve 204 will temporarily open when the external magnet 210 is positioned in proximity to the valve 204 and will close when the external magnet 210 is removed from the proximity of the valve 204. In certain embodiments, variable magnet strengths of external magnets may be used to control the dosage of the treatment substance. Additionally, an electromagnet may be used in place of the external magnet 210.

The use of a stop-check valve may prevent unintended dosing of the treatment substance when, for example, an accidental external force acts on the reservoir 202. The reservoir 202 is formed such that an increase in pressure of the reservoir 202 without an accompanying treatment substance release will not damage (i.e., rupture) the reservoir.

It is to be appreciated that the use of a magnetically activated stop-check valve is merely exemplary and that other types of valves may be used in alternative embodiments. For example, in alternative embodiments the valve 204 may be actuated (i.e., opened) in response to an electrical signal (e.g., piezoelectric valve). The electrical signal may be received from a portion of an auditory prosthesis (not shown) that is implanted with the delivery system 200 or the electrical signal may be received from an external device (e.g., an RF actuation signal received from an external sound processor, remote control, etc.). In other embodiments, manually applied (e.g., finger) force be also able to open the valve 204.

Once the treatment substance is released through valve 204, the treatment substance flows through the delivery tube 206 to the delivery device 208. The delivery device 208 operates as a transfer mechanism to transfer the treatment substance from the delivery tube 206 to the round window 121. The treatment substance may then enter the cochlea 140 through the round window 121 (e.g., via osmosis). The delivery device 208 may be, for example, a wick, a sponge, permeating gel (e.g., hydrogel), etc.

In accordance with further embodiments presented herein, the reservoir 202 may include a notification mechanism that transmits a signal or notification indicating that the reservoir 202 is substantially empty and/or needs refilled. For example, one or more electrode contacts (not shown) may be present and become electrically connected when the reservoir is substantially empty. Electronic components associated with or connected to the reservoir 202 may accordingly transmit a signal indicating that reservoir needs filled or replaced.

FIGS. 2A-2C illustrate a specific example in which the round window 121 is the target location. As noted above, the round window 121 is an exemplary target location and other target locations are possible in accordance with embodiments presented herein.

Figure 3A:
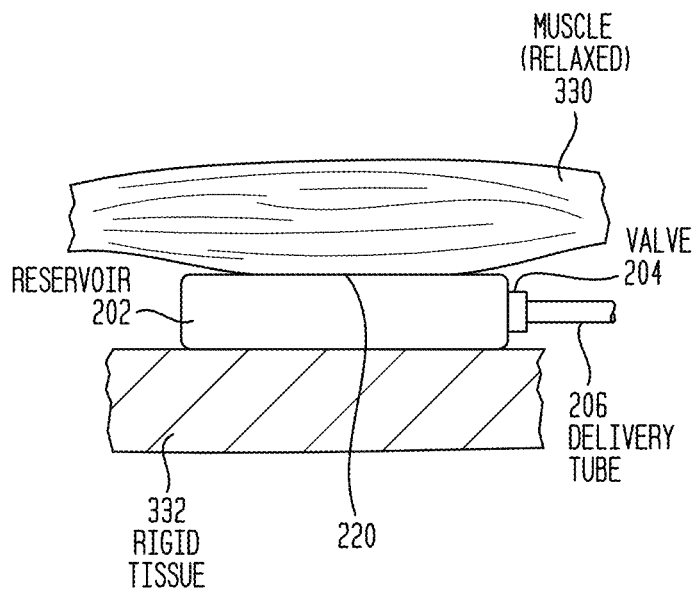
FIGS. 3A and 3B illustrate a reservoir in accordance with embodiments presented herein.
Figure 3B:
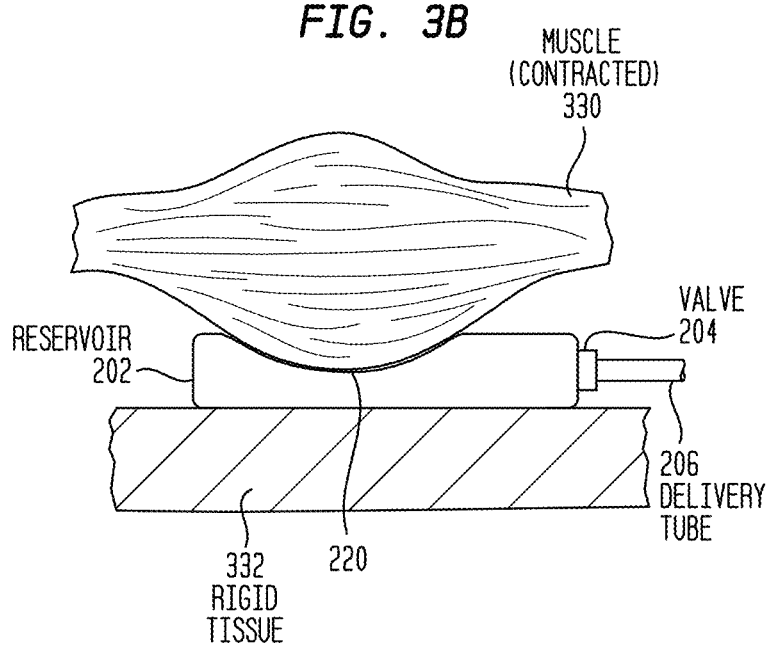

FIGS. 2A-2C illustrate an embodiment in which the reservoir 202 is positioned adjacent to the outer surface 229 of the recipient's skull so that an external force may be used to propel the treatment substance from the reservoir. FIGS. 3A and 3B illustrate another embodiment where an external force is not utilized to propel the treatment substance from the reservoir 202. More specifically, in the embodiments of FIGS. 3A-3B the reservoir 202 is positioned between a recipient's muscle 330 (e.g., temporalis (temporal muscle), jaw, etc.) and hard tissue 332 (e.g., bone, teeth, etc.). As shown in FIG. 3A, the muscle 330 may be in a relaxed state where little or no pressure is placed on the reservoir 202. As shown in FIG. 3B, the muscle 330 may alternatively be in a contracted state that compresses the reservoir 202. The compression of the reservoir 202 in response to the muscle contraction propels the treatment substance from the reservoir 202 into the delivery tube 206 via the valve 204. In certain circumstances, the muscle 330 may be contracted through mastication. As noted, the valve 204 may be a check valve or a stop-check valve (e.g., a magnetically operated valve).

Figure 4:
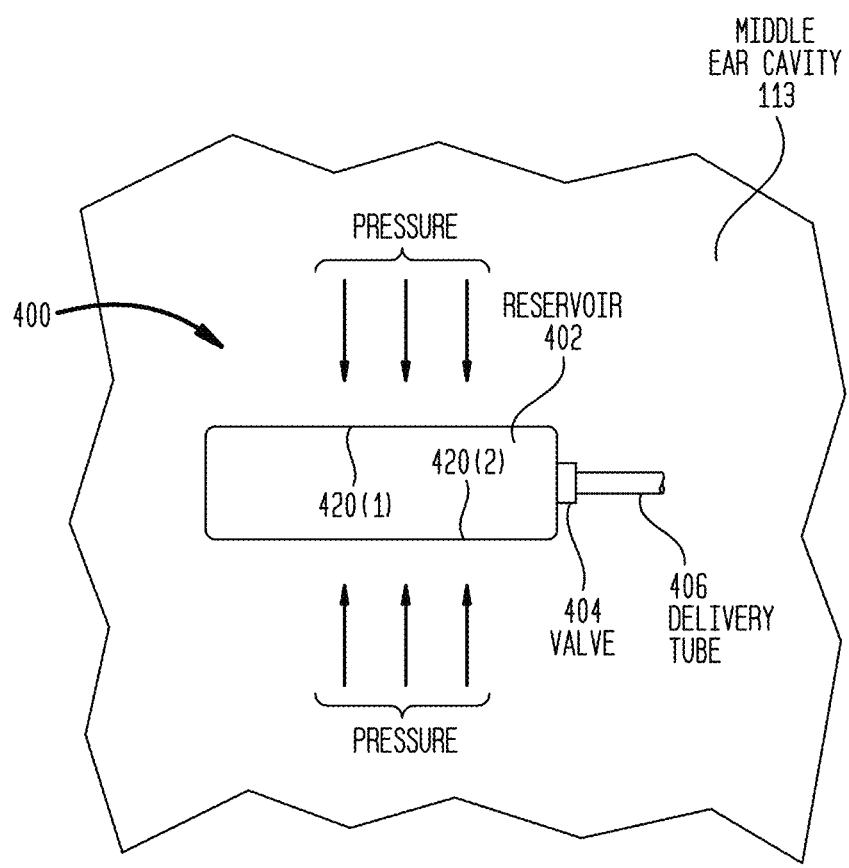
FIG. 4 illustrates another reservoir implanted in a recipient's middle ear cavity in accordance with embodiments of the present invention.

FIG. 4 illustrates a further embodiment where an external force may not be needed to propel a treatment substance from an implantable reservoir. More specifically, in delivery system 400 of FIG. 4, a reservoir 402 is positioned in the recipient's middle ear cavity 113. The reservoir 402 is, at least in part, formed from a resiliently flexible material that is deformable in response to pressurization of the middle ear cavity 113. FIG. 4 illustrates an example in which the reservoir 402 includes first and second opposing walls 420(1) and 420(2) that may deform in response to pressurization of the middle ear cavity 113. Deformation of the walls 420(1) and 420(2) pressurizes the interior of the reservoir 402 so as to propel the treatment substance through the valve 404 and into the delivery tube 406. Similar to the embodiments of FIGS. 2A-2B, the valve 404 may be a check valve or a stop-check valve (e.g., a magnetically operated valve).

In certain examples, ear equalization techniques can be used to pressurize the middle ear cavity 113 and deform the flexible reservoir 402. For example, the Valsalva maneuver (i.e., where the recipient pinches his/her nostrils closed and blows gently through the nose), the Frenzel maneuver (i.e., where the recipient performs a gentle Valsalva maneuver by breathing against pinched nostrils and swallowing at the same time), etc. may be used.

FIG. 4 illustrates an embodiment in which the reservoir 402 includes first and second opposing walls 420(1) and 420(2) that may deform in response to pressurization of the middle ear cavity 113. The reservoir 402 is secured within the middle ear cavity such that the pressure may act on both walls 420(1) and 420(2). In an alternative embodiment, the reservoir 402 may secured such that one wall of the reservoir 402 abuts hard tissue. In such embodiments, the reservoir wall that abuts the hard tissue may be compressible or substantially rigid.

FIG. 5A illustrates an embodiment where magnetic attraction is used to force a treatment substance from an implantable reservoir. More specifically, in the embodiment of FIG. 5A a magnetic element 534 is implanted abutting the outer surface 229 of the recipient's skull. The magnetic element 534 may be formed from a ferromagnetic or ferrimagnetic material. The ferromagnetic or ferrimagnetic material may be magnetized (i.e., a permanent magnet) or non-magnetized. FIG. 5A illustrates a specific embodiment in which the magnetic element 534 is a permanent magnet. The magnetic element 534 may be (optionally) secured to the superior portion 118 of recipient's temporal bone 115 using, for example, a bone screw (not shown) or another fixation mechanism (e.g., adhesive). Alternatively, the magnetic element 534 may be held in place by the recipient's tissue 219.

As shown, the reservoir 202 is implanted so as to abut an externally-facing surface 525 of the magnetic element 534 (i.e., a surface facing away from the recipient's temporal bone 115). The reservoir 202 may be secured to the magnetic element 534 and/or the recipient's temporal bone using one or more fixation mechanisms described further below or may be held in place by the recipient's tissue 219.

In the embodiment of FIG. 5A, an external magnet 536 may be placed adjacent to the recipient's tissue 219 that at least partially covers the reservoir 202. The poles of the external magnet 536 and the magnetic element 534 are oriented so that the external magnet 536 and the magnetic element 534 will be magnetically attracted to one another when in proximity to one another. As shown by arrows 538 in FIG. 5A, the mutual attraction between the external magnet 536 and the magnetic element 534 compresses the recipient's tissue 219 adjacent to the reservoir 202. The compression of the tissue, in turn, compresses the wall 220 of the reservoir 220. The positioning of the reservoir 202 abutting the magnetic element 435 and the superior portion 118 of the mastoid 115 provides a rigid surface that counters the compression of the tissue 219. As a result, a pressure change occurs in the reservoir 202 so as to propel a portion of the treatment substance out of the reservoir through valve 204.

As noted, the valve 204 may be a check valve or a stop-check valve (e.g., a magnetically operated valve). In embodiments in which the valve 204 is a magnetically operated valve, the external magnet 536 may be configured so as to compress the reservoir 202 and additionally open valve 204.

The magnetic element 534 and external magnet 536 may have a variety of shapes and sizes (e.g., cylindrical, square, rectangular, etc.). In certain embodiments, the magnetic element 534 and external magnet 536 have corresponding generally annular shapes to enhance the alignment of the magnetic elements with one another.

FIG. 5B illustrates another embodiment where magnetic attraction is used to force a treatment substance from an implantable reservoir. More specifically, in the embodiment of FIG. 5B a reservoir 502 comprises a first end plate 513 connected to a second plate 515 by a substantially flexible outer wall 519. The end plates 513 and 515 may be, for example, circular, oval, square, rectangular, etc. so as to, along with flexible outer wall 519, form a closed body in which a treatment substance may be disposed. One or both of the end plates 513 and 515 may be formed from ferromagnetic or ferrimagnetic material (magnetized or non-magnetized) such that when an external magnet 537 is in proximity to the reservoir 502, the treatment substance may be forced through valve 204. For example, in one such embodiment the end plates 513 and 515 may be configured such that the presence of the magnet 537 causes plate 513 to be forced away from the magnet 537 (as shown by arrows 521), while the end plate 515 is pulled towards the magnet 537 (as shown by arrows 523). This "squeezing" action produced by the presence of external magnet 537 forces the treatment substance through valve 204.

FIGS. 2A through 5B illustrate embodiments in which drugs that are forced from an implantable reservoir pass through a valve and directly into a delivery tube. FIG. 6 illustrates an embodiment where a secondary reservoir 640 is added to enable extended treatment substance release. More specifically, in the embodiment of FIG. 6, when the treatment substance is released from reservoir 202, the treatment substance passes through valve 204 and into a connector tube 642. The distal end 643 of the connector tube 642 is connected to the secondary reservoir 640 such that application of the external force 216 propels the treatment substance from reservoir 202 into the secondary reservoir 640. A valve 644 at the output of the secondary reservoir 640 may be configured to release the treatment substance from the secondary reservoir to the delivery tube 206 at a predetermined rate (e.g., at certain time periods). As such, the arrangement of FIG. 6 can utilize the secondary reservoir 640 to deliver the treatment substance to the delivery device 208 (FIG. 2C) over a period of time without the need for application of additional external forces 216.

FIG. 6 illustrates the use of a secondary reservoir and a primary reservoir positioned adjacent to the outer surface 229 of the recipient's skull. It is to be appreciated that a secondary reservoir may also be used in other embodiments presented herein (e.g., with a primary reservoir positioned in the middle ear cavity).

Figure 7:
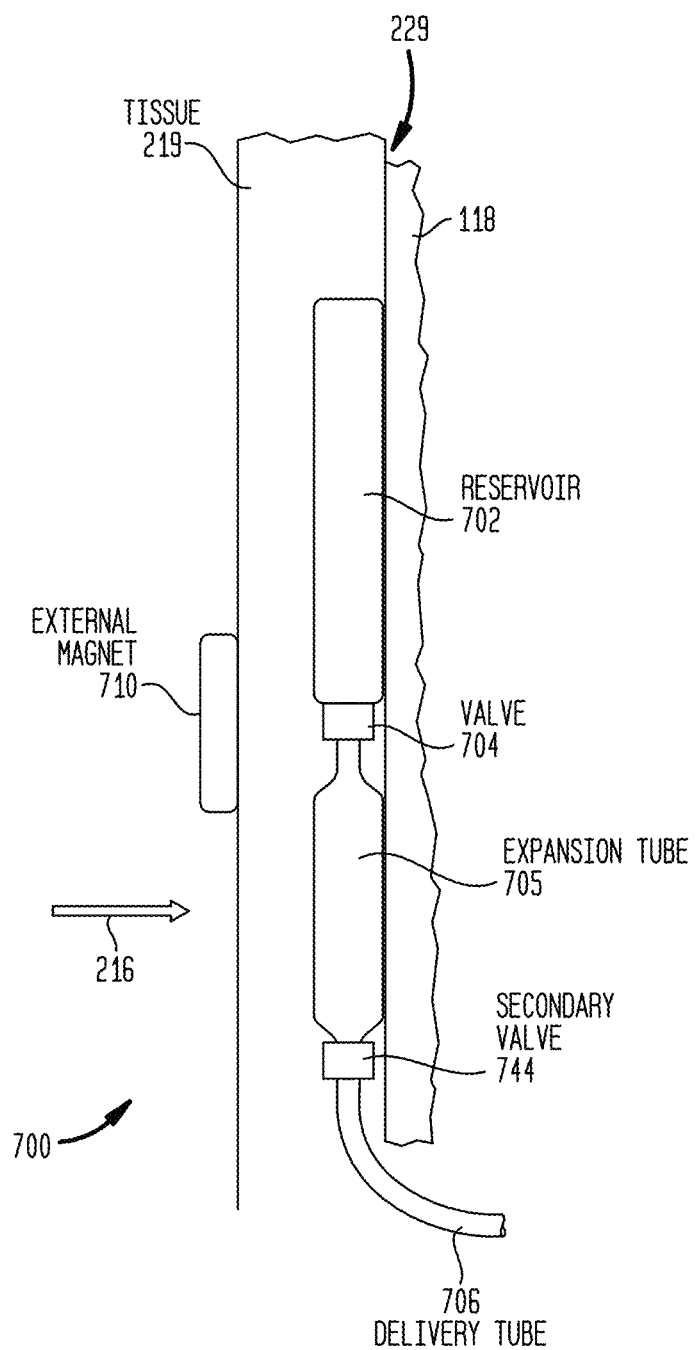
FIG. 7 illustrates another delivery system in accordance with embodiments presented herein.

FIG. 7 illustrates another embodiment where the external force is applied to a section of tubing rather than a reservoir. More specifically, FIG. 7 illustrates a delivery system 700 that comprises a reservoir 702, a valve 704, an expansion tube 705, a delivery tube 706, a secondary valve 744, and a delivery device (not shown). The delivery system 700 may include, or operate with, an external magnet 710.

In the embodiment of FIG. 7, the reservoir 702 and the expansion tube 705 are positioned underneath the recipient's tissue 219 adjacent to outer surface 229 of the recipient's skull. The reservoir 702 is at least partially filled with a treatment substance for delivery to the inner ear 107 of the recipient. The reservoir 702 may include a needle port (not shown) so that the reservoir can be refilled via a needle injection through the skin or the reservoir 702 may be explanted and replaced with another reservoir that is configured to be at least partially filled with a treatment substance.

The expansion tube 705 is a tubing section formed from a resiliently flexible (e.g., elastomer) element configured to compress in response to application of an external force 216 applied, for example, manually or semi-manually as described above. The positioning of the expansion tube 705 adjacent the superior portion 118 of the mastoid 115 provides a rigid surface that counters the external force 216. As a result, that application and subsequent removal of the external force 216 causes rapid pressurization and depressurization of the expansion tube 705 so as to pull the treatment substance from reservoir 702 through the valve 704. As a result, the expansion tube 705 expands as it is substantially or partially filled with the treatment substance.

It is to be appreciated that the positioning of expansion tube 705 adjacent the superior portion 118 of the mastoid 115 is merely illustrative. The expansion tube 705 may be positioned to other natural or surgical implanted semi-rigid elements so as to enable rapid pressurization and depressurization of the expansion tube 705.

The expansion tube 705 may fill up to a certain volume in response to the repeated application and removal of the external force 216. The valve 744 at the output of the expansion tube 705 may be configured to release the treatment substance from the secondary reservoir to the delivery tube 706 at a predetermined rate (e.g., at certain time periods). As such, the arrangement of FIG. 7 can utilize the expansion tube 705 to deliver the treatment substance to the delivery device over a period of time without the need for application of additional external forces 216.

As noted, the treatment substance is released from the reservoir 702 through the valve 704. The valve 704 may be a check valve that allows the treatment substance to pass there through in one direction only. This assures that released treatment substances do not back-flow into the reservoir 702. In certain embodiments, the valve 704 is a valve that is configured to open in response to the pressure change in the expansion tube 705. In certain embodiments, the valve 704 is a stop-check valve that includes an override control to stop flow regardless of flow direction or pressure. For example, the valve 704 may be a stop-check value that is controlled by the external magnet 710. In such embodiments, the valve 704 will temporarily open when the external magnet 710 is positioned in proximity to the valve 704 and will close when the external magnet 710 is removed from the proximity of the valve 704. The use of a stop-check valve may prevent unintended dosing of the treatment substance when, for example, an accidental external force acts on the expansion tube 705.

It is to be appreciated that the use of magnetically activated stop-check valve is merely exemplary and that other types of valves may be used in alternative embodiments. For example, in alternative embodiments the valve 704 may be actuated (i.e., opened) in response to an electrical signal. The electrical signal may be received from a portion of an auditory prosthesis (not shown) that is implanted with the delivery system 700 or the electrical signal may be received from an external device (e.g., an RF actuation signal received from an external sound processor, remote control, etc.).

Figure 8A:
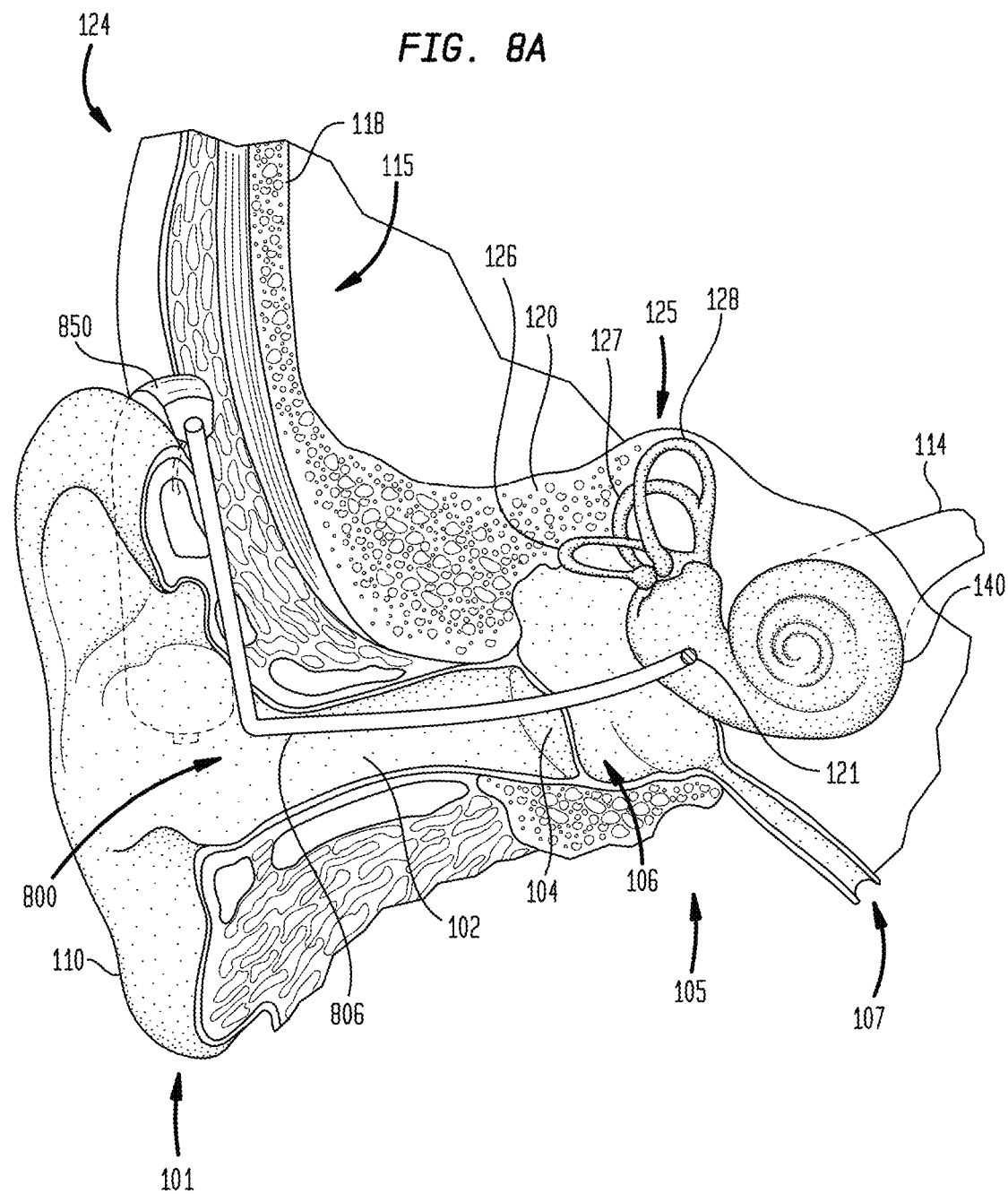
FIG. 8A illustrates a further delivery system in accordance with embodiments presented herein.

FIGS. 2A-7 illustrate embodiments that utilize an implantable reservoir and a passive actuation mechanism to transfer treatment substances from the reservoir to a target location. In alternative embodiments, treatment substances are delivered to a recipient's middle ear/inner ear using a substantially external system where the reservoir and actuation unit (e.g., pump) need not be implanted in the recipient. More specifically, FIGS. 8A-8C illustrate a delivery system 800 comprising an external component 850, a delivery tube 806, and delivery device 808. The external component 850 is a behind-the-ear component that is configured to be worn on the outer ear 101 of the recipient.

As shown in FIG. 8B, the external component 850 comprises a reservoir 802 that is configured to be at least partially filled with a treatment substance. The external component 850 also comprises a valve 804 (e.g., check valve), a pump 852 and a power source (e.g., battery) 854. In operation, the pump 852 propels the treatment substance in the reservoir 802 through the valve 804 and into the delivery tube 806.

The delivery tube 806 has a proximal end 812 (FIG. 8B) that is fluidically coupled to the valve 804, and a distal end 814 (FIG. 8C) that is fluidically coupled to the round window 121. As shown in FIGS. 8A and 8C, the delivery tube 806 extends from the external component 850 and into the recipient's ear canal 102. The delivery tube 806 also extends through the recipient's tympanic membrane 104 to the round window 121. In particular, the delivery tube 806 passes through a surgically formed opening within the tympanic membrane 104. A surgically placed grommet 856 seals the opening in the tympanic membrane 104 around the delivery tube.

Once the treatment substance is released through valve 804, the treatment substance flows through the delivery tube 806 to the delivery device 808 (passing through the ear canal 102 and the tympanic membrane 104). The delivery device 808 operates as a transfer mechanism to transfer the treatment substance from the delivery tube 806 to the round window 121. The treatment substance may then enter the cochlea 140 through the round window 121 (e.g., via osmosis). The delivery device 808 may be, for example, a wick, a sponge, permeating gel (e.g., hydrogel), etc.

External components, such as behind-the-ear components, are used with a number of implantable auditory prostheses. It is to be appreciated that the external component 850 of FIGS. 8A and 8B may also include the components of an external component used with an implantable auditory prosthesis (e.g., sound processor, sound input element, etc.). That is, external component 850 may be integrated with the components of an external component of an implantable auditory prosthesis.

Figure 9:
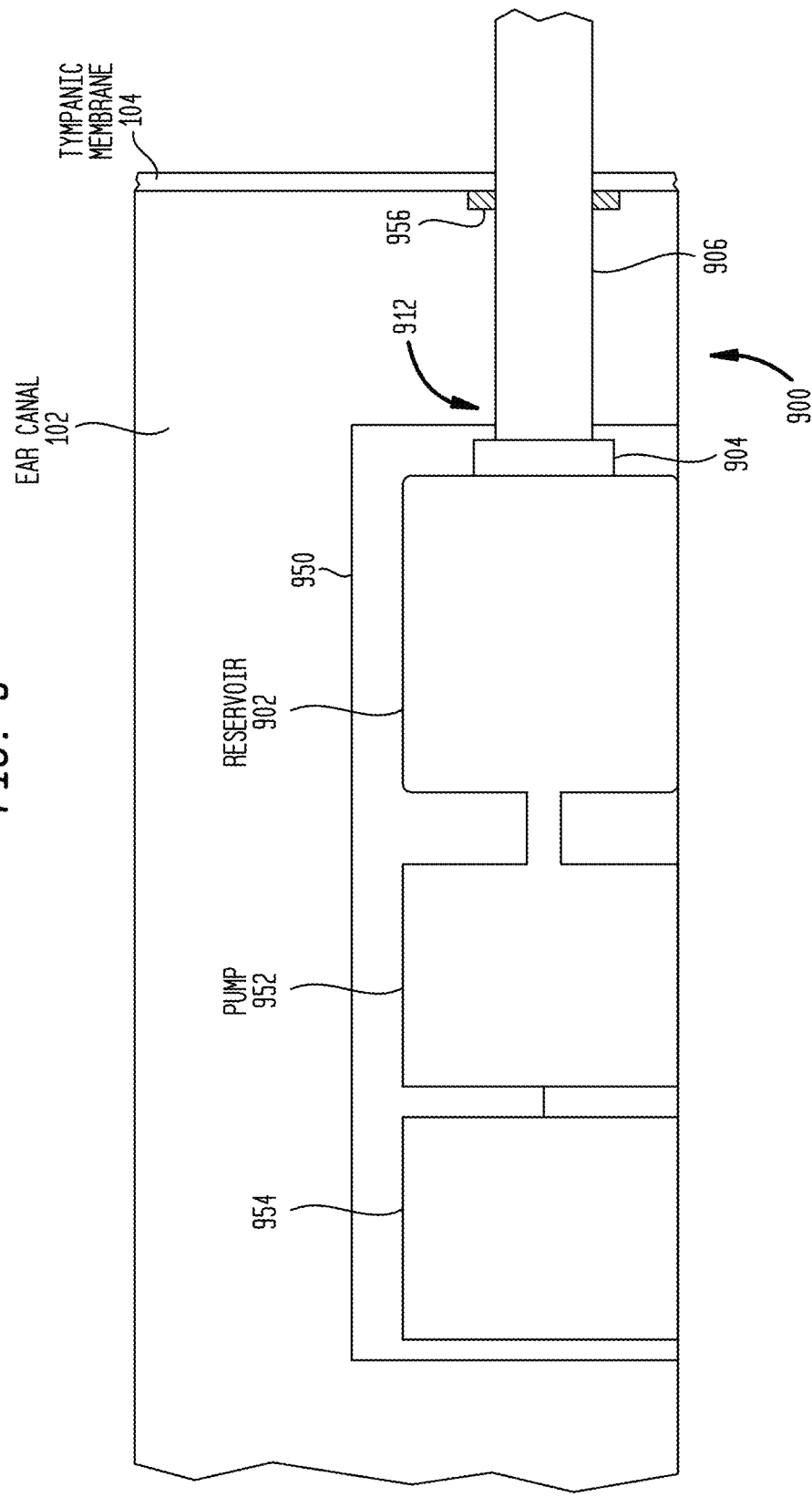
FIG. 9 illustrates another delivery system in accordance with embodiments presented herein.

FIG. 9 illustrates another delivery system 900 comprising an external component 950, a delivery tube 906, and a delivery device (not shown). The external component 950 is an in-the-ear component positioned in the pinna 110 or ear canal 102 of the recipient.

The external component 950 comprises a reservoir 902 that is configured to be at least partially filled with a treatment substance. The external component 950 also comprises a valve 904 (e.g., check valve), a pump 952, and a power source 954. In operation, the pump 952 propels the treatment substance in the reservoir 902 through the valve 904 and into the delivery tube 906.

The delivery tube 906 has a proximal end 912 that is fluidically coupled to the valve 904 and a distal end (not shown) that is fluidically coupled to the round window 121. The delivery tube 906 extends from the external component 950 through the recipient's tympanic membrane 104 to the round window 121. In particular, the delivery tube 906 passes through a surgically formed opening within the tympanic membrane 104. A surgically placed grommet 956 seals the opening in the tympanic membrane 104 around the delivery tube.

Once the treatment substance is released through valve 904, the treatment substance flows through the delivery tube 906 to a delivery device (not shown) by passing through the tympanic membrane 104. The delivery device may be substantially similar to delivery device 808 of FIG. 8 and operates as a transfer mechanism to transfer the treatment substance from the delivery tube 906 to the round window 121.

Delivery systems in accordance with embodiments presented herein are intended for delivery of treatment substances to a target location within a recipient. As noted, the target location may be, for example, the recipient's middle ear, inner ear, round window, oval window, through a cochleostomy, on/at a cochleostomy, etc. In certain examples, the target location may be a portion of the inner ear that enables the treatment substance to travel to a further location such as, for example, the auditory brainstem or brain. In accordance with certain arrangements, the delivery systems may include one or more fixation mechanisms that retain various components of the delivery systems at a selected implanted location to ensure that the treatment substance is properly delivered to the target location. FIGS. 10A-13B illustrate fixation mechanisms that may be used in accordance with embodiments presented herein.

Figure 10A:
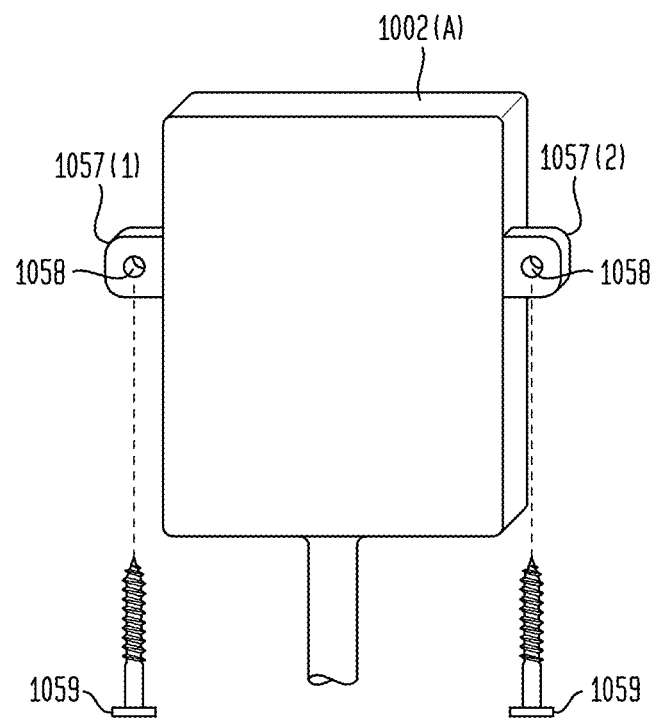
FIGS. 10A-10C illustrate arrangements for securing components of a delivery system within a recipient.

FIGS. 10A-10D illustrate mechanisms for securing components of an implantable delivery system to tissue of a recipient. More specifically, FIG. 10A illustrates a reservoir 1002(A) that includes first and second anchor loops 1057(1) and 1057(2). The anchor loops 1057(1) and 1057(2) may be integrated with the reservoir 1002 or attached to the reservoir using, for example, a bonding agent (e.g., bone cement or other biocompatible adhesive). In certain embodiments, the anchor loops 1057(1) and 1057(2) are formed from a resiliently flexible material (e.g., a similar material used to form the reservoir 1002(A)). In other embodiments, the anchor loops 1057(1) and 1057(2) are formed from a substantially rigid material (e.g., titanium).

The anchor loops 1057(1) and 1057(2) each include an aperture 1058. The reservoir 1002 is configured to be positioned adjacent to the recipient's tissue. Bone screws 1059 or other fasteners may then be inserted through the apertures 1058 and into the tissue. In this way, the bone screws secure the reservoir 1002(A) in position. In alternative embodiments, the anchor loops 1057(1) and 1057(2) may be replaced with pads or other members that enable the reservoir 1002(A) to be secured to the recipient using, for example, a bonding agent (e.g., bone cement or other biocompatible adhesive), sutures, etc.

Figure 10B:
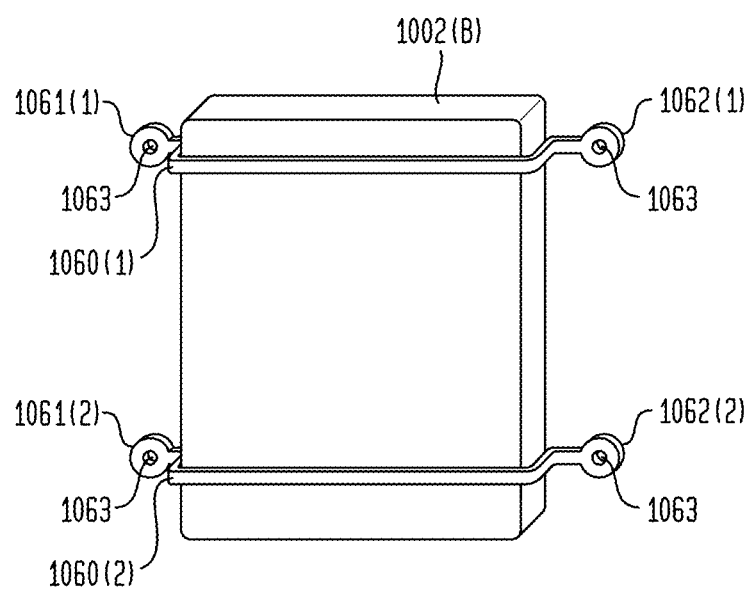

FIG. 10B illustrates another reservoir 1002(B) with a first fastening bracket 1060(1) and a second fastening bracket 1060(2). The first fastening bracket 1060(1) includes an anchor loop 1061(1) at a first end of the bracket and an anchor loop 1062(1) at a second end of the bracket. The second fastening bracket 1060(2) includes an anchor loop 1061(2) at a first end of the bracket and an anchor loop 1062(2) at a second end of the bracket. Each of the anchor loops 1061(1), 1061(2), 1062(1), and 1062(2) include an aperture 1063.

The reservoir 1002(B) is configured to be positioned adjacent to the recipient's tissue. The fastening brackets 1060(1) and 1060(2) are configured to fit around the reservoir 1002(B) and bone screws 1059 (FIG. 10A) or other fasteners may then be inserted through the apertures 1058 and into the tissue. In this way, the brackets 1060(1) and 1060(2) secure the reservoir 1002(B) in position. In alternative embodiments, the anchor loops 1061(1), 1061(2), 1062(1), and 1062(2) may be replaced with pads or other members that enable the reservoir 1002(B) to be secured to the recipient using, for example, a bonding agent (e.g., bone cement or other biocompatible adhesive), sutures, etc.

For ease of illustration, FIGS. 10A and 10B illustrate anchor loops and brackets, respectively, with reference to implantable reservoirs. It is to be appreciated that these fixation mechanisms may be used with other implantable components of a delivery system to facilitate attachment of those components to a recipient's tissue.

Figure 10C:
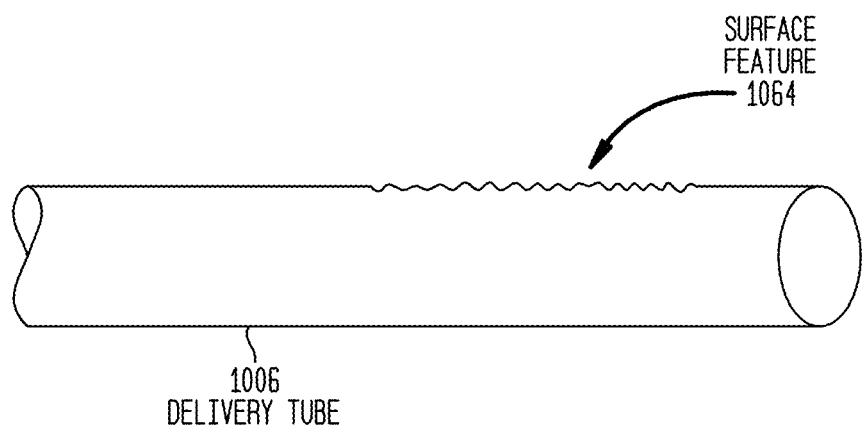

FIG. 10C illustrates a fixation mechanism for the distal end of a delivery tube 1006 of a delivery system. In this embodiment, the delivery tube 1006 includes surface features 1064 that are configured to facilitate attachment of a bonding agent (e.g., bone cement or other biocompatible adhesive) to the surface of the delivery tube or to allow natural retention of the tube by body tissue, fibrotic response, etc. The bonding agent then secures the distal end of the delivery tube 1006 to the recipient's tissue.

The surface features 1064 (i.e., the fixation mechanism) may have a number of different configurations. In one embodiment, the surface features comprise a plurality of recesses in the form of spaced grooves or troughs and/or ridges. The grooves/ridges may have different shapes and configurations. For example, grooves/ridges may have cross-sectional shapes that are rectangular, triangular, trapezoidal, etc. It is also to be appreciated that grooves in alternative embodiments may have geometries that include different undercut regions. For example, alternative grooves may be T-shaped, J-shaped, dovetailed, frustoconical, etc. The undercut regions may function to create a mechanical lock, or an interlock between a bonding agent and the surface of the delivery tube 1006.

In another embodiment, the surface features 1064 comprise a collection of depressions and/or protrusions. The protrusions may have a number of different shapes (e.g., parabolic, square, rectangular, arcuate, etc.).

In a still other embodiment, the surface features 1064 comprise include a plurality of recesses in the form of pores. The pores may have irregular shapes that potentially result in mechanical locking. That is, the irregular shape of the pores may cause the bonding agent and/or tissue to undergo one or more turns when the bonding agent fills the pore For ease of illustration, FIG. 10C illustrates surface features in/on the surface of a delivery tube. It is to be appreciated that these and other surface features may be used in/on the surfaces of other implantable components of a delivery system to facilitate attachment of a bonding agent thereto for subsequent securement to tissue.

Figure 11:
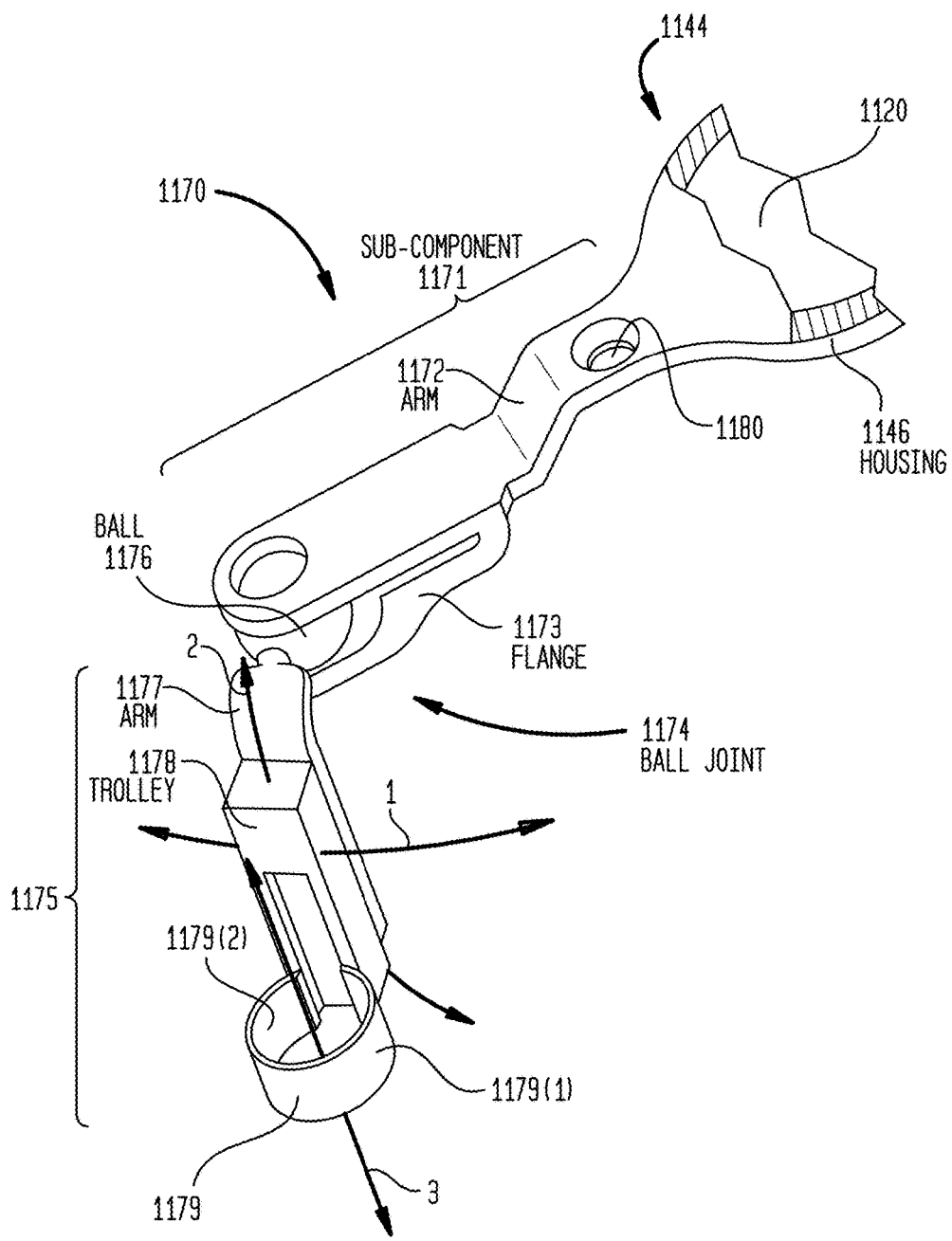
FIG. 11 illustrates a delivery tube positioning mechanism in accordance with embodiments presented herein.

FIG. 11 illustrates a delivery tube positioning mechanism 1170 that may be used in accordance with embodiments presented herein to locate the distal end of a delivery tube (not shown in FIG. 11) adjacent to a target location (e.g., the round window 121). Delivery tube positioning mechanism 1170 comprises two sub-components, namely extension arm 1171 and extension arm 1175.

Sub-component 1171 includes arm 1172 which is an integral part of housing 1146 (where the cross-hatching of housing 1146 seen in FIG. 11 corresponds to the wall of the housing). Arm 1172 may be part of the same casting forming at least part of housing 1146 (i.e., the arm 1172 and at least a portion of the housing 1146 form a monolithic component), although in an alternate exemplary embodiment, arm 1172 may be a separate component that is attached to the housing 1146 (e.g., via laser welding). In an exemplary embodiment, the casting may be made partially or totally out of titanium. In this regard, it is noted that the delivery tube positioning mechanism 1170 may be partially or totally formed from titanium, and the housing 1146 may be formed from a different material. Sub-component 1171 also includes flange 1173 which forms a female portion of ball joint 1174.

The delivery tube positioning mechanism 1170 further includes subcomponent 1175. Sub-component 1175 comprises the male portion of the ball joint 1174, in the form of a ball 1176, arm 1177, trolley 1178 and delivery tube support 1179. Delivery tube support 1179 is depicted as being in the form of a collar, and receives and otherwise holds a delivery tube therein. For ease of illustration, the delivery tube has been omitted from FIG. 11.

Ball joint 1174 permits the ball 1176 of sub-component 1175 to move within the female portion, thereby permitting sub-component 1175 to articulate relative to sub-component 1171. This articulation permits the delivery tube to likewise articulate. Ball joint 1174 also enables the delivery tube to be positioned at an adjustably fixed location relative to the target location. In an exemplary embodiment, the ball joint 1174 permits the location of the delivery tube to be adjustable in two degrees of freedom, represented by arrows 1 and 2 (first and second degrees of freedom, respectively), in FIG. 11. In some embodiments, the joint may permit the location of the delivery tube to be adjustable in only one degree of freedom or in more than two degrees of freedom.

While delivery tube positioning mechanism 1170 is depicted with a ball joint 1174, other types of joints may be utilized. By way of example, the joint may comprise a malleable portion of a structural component of the delivery tube positioning mechanism 1170 that permits the delivery tube to be positioned as just detailed or variations thereof. In an exemplary embodiment, the joint is an elastically deformable portion or plastically deformable portion or is a combination of elastically deformable and plastically deformable portions so as to enable the adjustment of the location of the delivery tube in the at least one degree of freedom.

The collar 1179 has an exterior surface 1179(1) and an interior surface 1179(2), configured to receive the delivery tube. The interior diameter of the collar, formed by interior surface 1179(2) is approximately the same as the outer diameter of the cylindrical body of the delivery tube.

As noted, delivery tube support 1179 secures the delivery tube to the delivery tube positioning mechanism 1170. This removable securement may be, in some embodiments, sufficient to prevent the delivery tube from substantially moving from the retained location in the delivery tube support 1179. In an exemplary embodiment, interlock between the delivery tube support 1179 and the delivery tube is provided by an interference fit between inner surface 1179(1) and the delivery tube. In an alternate embodiment, interlock between the delivery tube support 1179 and the delivery tube is implemented as corresponding mating threads on inner surface 1179(1) and the delivery tube.

In another embodiment, O-rings or the like may be used to secure the delivery tube within the delivery tube support 1179. Grooves on the delivery tube and/or on the collar may be included to receive the O-ring. Alternatively, compression of the O-ring between the delivery tube and the collar provides sufficient friction to retain the delivery tube in the delivery tube support 1179.

In a further embodiment, delivery tube support 1179 or the delivery tube includes a biased extension that is adjusted against the bias to insert the delivery tube into the support. The extension may engage a detent on the opposing surface to interlock the delivery tube and the support. Other embodiments include protrusions and corresponding channels on opposing surfaces of the delivery tube and the delivery tube support 1179. An exemplary embodiment includes a spring-loaded detent that interfaces with a detent receiver of the opposing surface to hold the delivery tube in the delivery tube support 1179. Adhesive may be used to interlock the delivery tube in the delivery tube support 1179.

The trolley 1178, which is rigidly connected to delivery tube support 1179, is configured to move linearly in the direction of arrow 3 parallel to the longitudinal direction of extension of arm 1177. In this exemplary embodiment, arm 1177 includes tracks with which trolley 1178 interfaces to retain trolley 1178 to arm 1177. These tracks also establish trolley 1178 and arm 1177 as a telescopic component configured to enable the adjustment of the location of delivery tube support 1179, and thus the delivery tube when received therein, in at least one degree of freedom (i.e., the degree of freedom represented by arrow 3). It is noted that other embodiments may permit adjustment in at least two or at least three degrees of freedom. Thus, when the trolley component is combined with the aforementioned joint 1174, the delivery tube positioning mechanism 1170 enables the location of the delivery tube to be adjustable in at least two or at least three degrees of freedom.

Movement of the trolley 1178 along arm 1177 may be accomplished via a jack screw mechanism where the jack screw is turned via a screw driver or a hex-head wrench. Movement of the trolley 1178 may also or alternatively be achieved via application of a force thereto that overcomes friction between the trolley 1178 and the arm 1177. Any device, system or method that permits trolley 1178 to move relative to arm 1172 may be used in some embodiments detailed herein and variations thereof.

It may be seen that arm 1172 of delivery tube positioning mechanism 1170 includes screw hole 1180. Screw hole 1180 is configured to receive a bone screw (not shown in FIG. 11) for securing of the delivery tube positioning mechanism 1170 to the recipient's tissue. While screw hole 1180 is depicted as being located on (in) arm 1172, in other embodiments, screw holes may be located elsewhere on the delivery tube positioning mechanism 1170.

Figure 12A:
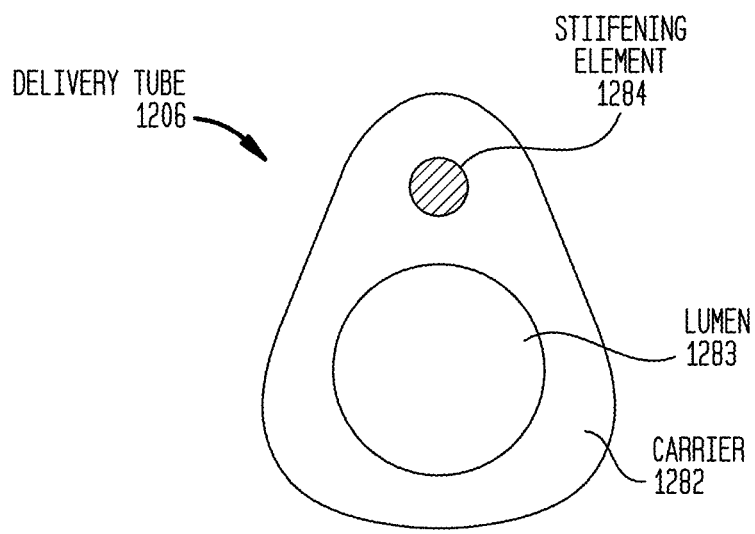
FIGS. 12A and 12B illustrate a delivery tube in accordance with embodiments presented herein.
Figure 12B:
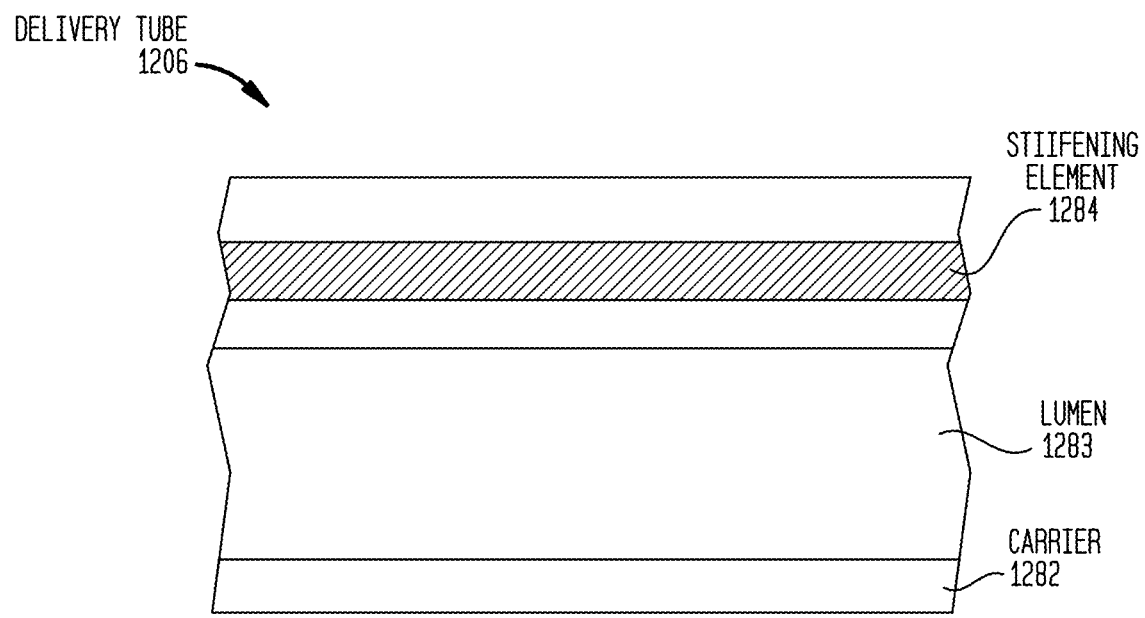

In certain embodiments, the fixation mechanisms used to retain a distal end of a delivery tube in place at a target location are the physical properties of the delivery tube. For example, FIGS. 12A and 12B are cross-sectional views illustrating a delivery tube 1206 that is conformable, but also has sufficient rigidity to provide stability and to remain in a selected position and configuration. FIG. 12A illustrates a lateral cross-sectional view of the delivery tube 1206, while FIG. 12B illustrates an elongate cross-sectional view of the delivery tube 1206.

The delivery tube 1206 comprises a carrier 1282 that forms a lumen 1283. A treatment substance is delivered from a reservoir to a target location through the lumen 1283. The carrier 1282 may be formed from, for example, a biocompatible elastomer (e.g., silicone rubber) or similar substantially comfortable/pliable material. The carrier 1282 has material properties so as to prevent egress of a treatment substance from the lumen 1283 as well as to prevent the ingress of bodily fluids.

The delivery tube 1206 also comprises a stiffening element 1284 extending along all or part of the elongate length of the delivery tube. In the embodiments of FIGS. 12A and 12B, the stiffening element 1284 is an elongate wire (e.g., platinum, titanium, etc.) embedded in the carrier 1382. In other embodiments, the stiffening element 1284 may be formed from a polymer material. In general, the carrier 1282 and stiffening element 1284 are conformable to a selected configuration (e.g., location, position, orientation, etc.). The stiffening element 1284 has mechanical properties (e.g., rigidity, malleability, etc.) such that the delivery tube 1206 remains in the selected configuration.

Figure 13A:
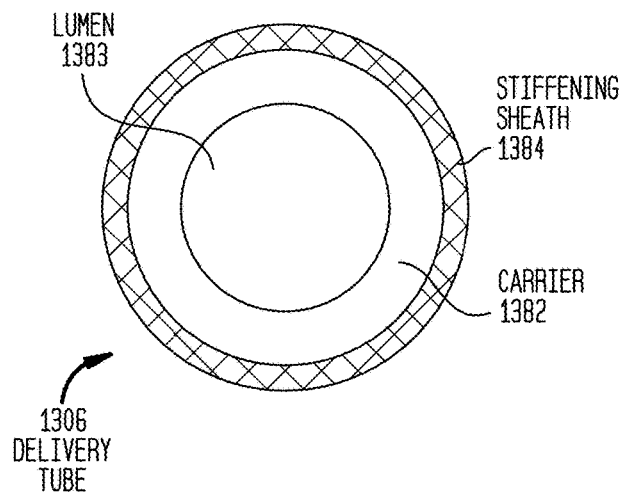
FIGS. 13A and 13B illustrate another delivery tube in accordance with embodiments presented herein.
Figure 13B:
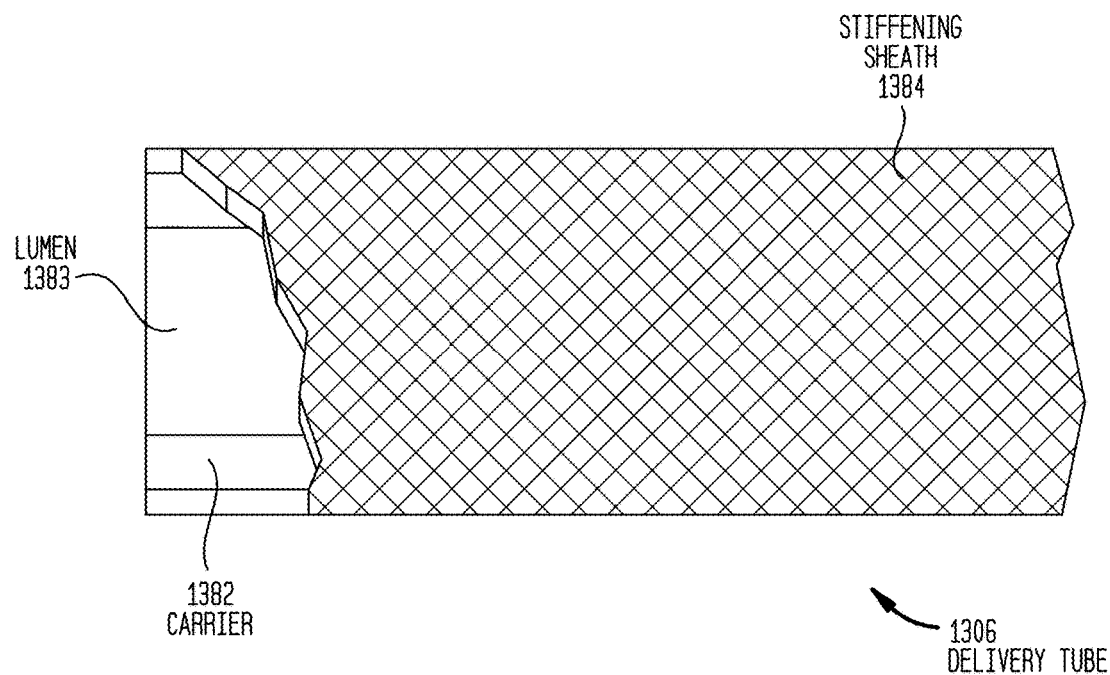

FIGS. 13A and 13B illustrate another delivery tube 1306 that is conformable, but also has sufficient rigidity to provide stability and to remain in a selected position. The delivery tube 1306 comprises a carrier 1382 surrounded by a stiffening sheath 1384. FIG. 13A illustrates a lateral cross-sectional view of the delivery tube 1306, while FIG. 13B is a side view from which part of the stiffening sheath 1384 has been omitted.

The carrier 1382 forms a lumen 1383 that carries a treatment substance from a reservoir to a target location. The carrier 1282 may be formed from, for example, a biocompatible elastomer or similar substantially conformable/pliable material. The carrier 1382 has material properties so as to prevent egress of a treatment substance from the lumen 1383 as well as to prevent the ingress of bodily fluids.

The stiffening sheath 1384 substantially surrounds the carrier 1382 and extends along all or part of the elongate length of the delivery tube. In the embodiments of FIGS. 13A and 13B, the stiffening sheath is a mesh (e.g., titanium, wire, polymer, etc.). In general, the carrier 1382 and stiffening sheath 1384 are conformable to a selected configuration. The stiffening sheath 1384 has mechanical properties (e.g., rigidity, malleability, etc.) such that the delivery tube 1306 remains in the selected configuration.

It is to be appreciated the embodiments of FIGS. 12A-13B are illustrative and other stiffening elements or mechanisms may be used to form a delivery tube with physical properties that assist in retention of the distal end of the delivery tube at a target location. For example, the carrier of the delivery tube may be formed from a flexible material that protects against external force (e.g., using shape memory materials).

One potential issue with certain delivery systems is the accretion (build-up) of undelivered treatment substance particles within the system. For example, if the delivery of a treatment substance is started and is then stopped for a period of time (e.g., in cases of pain relief or to combat infections), portions of the treatment substance may remain in the system outside of the reservoir. These undelivered portions of the treatment substance outside of the reservoir may precipitate (e.g., crystalize) and potentially clog the system at the delivery tube, the delivery device, etc. so as to inhibit subsequent delivery of the treatment substance. As noted above, certain embodiments presented herein are directed to accretion prevention (anti-accretion) mechanisms that prevent the buildup of precipitated particles within a delivery system that can inhibit subsequent treatment substance delivery. FIG. 14 illustrates an example delivery system 1400 that includes a flushing module 1475 that operates as an anti-accretion mechanism.

The delivery system 1400 is similar to the arrangement of FIG. 5 where a magnetic attraction is used to propel a treatment substance from an implantable reservoir. More specifically, the delivery system 1400 comprises a magnetic element 1434 implanted abutting a first section of the outer surface 229 of the recipient's skull. The magnetic element 1434 may be formed from a ferromagnetic or ferrimagnetic material and may be magnetized (i.e., a permanent magnet) or non-magnetized. FIG. 14 illustrates an embodiment in which the magnetic element 1434 is a permanent magnet.

The magnetic element 1434 may be secured to the superior portion 118 of recipient's temporal bone 115 using, for example, a bone screw (not shown) or another fixation mechanism (e.g., adhesive).

As shown, a treatment substance reservoir 1402 is implanted so as to abut an externally-facing surface 1425 of the magnetic element 1434 (i.e., a surface facing away from the recipient's temporal bone 115). The treatment substance reservoir 1402 may be secured to the magnetic element 1434 and/or the recipient's temporal bone using one or more fixation mechanisms described elsewhere herein. The treatment substance reservoir 1402 is at least partially filled with a treatment substance.

The flushing module 1475 comprises a second magnetic element 1444 implanted abutting a second section of the outer surface 229 of the recipient's skull. The magnetic element 1444 may be formed from a ferromagnetic or ferrimagnetic material and may be magnetized or non-magnetized. FIG. 14 illustrates an embodiment in which the magnetic element 1444 is a permanent magnet. The magnetic element 1444 may be secured to the superior portion 118 of recipient's temporal bone 115 using, for example, a bone screw (not shown) or another fixation mechanism.

As shown, a flushing reservoir 1452 is implanted so as to abut an externally-facing surface 1455 of the magnetic element 1444 (i.e., a surface facing away from the recipient's temporal bone 115). The treatment substance reservoir 1402 may be secured to the magnetic element 1434 and/or the recipient's temporal bone using one or more fixation mechanisms described elsewhere herein. As described further below, the flushing reservoir 1452 is at least partially filled with a flushing solution (e.g., saline).

The treatment substance reservoir 1402 is fluidically coupled to the proximal end of a connector tube 1456 via a one-way valve 1458. Similarly, the flushing reservoir 1452 is fluidically coupled to a proximal end of connector tube 1466 via a one-way valve 1468. The connector tubes 1456 and 1466 terminate at a three-port valve 1470. That is, the valve 1470 has a first port connected to the connector tube 1456, a second port connected to the connector tube 1466, and third port connected to a delivery tube 1406.

In general, the valves 1458 and 1468 allow a treatment substance or flushing solution, respectively, to pass from the respective reservoirs to the valve 1470. The valve 1470 is configured to allow either the treatment substance or the flushing solution to pass to the delivery tube 1406. The valve 1470 is configured to prevent the treatment substance from passing into the connector tube 1466 and to prevent the flushing solution from passing into the connector tube 1456.

It is to be appreciated that the use of a three-port valve 1470 is merely illustrative and that other valves may be used in alternative embodiments. For example, in certain embodiments, the three-port valve 1470 may be replaced with separate one-way valves positioned at the distal end of each of the connector tunes 1456 and 1466.

In the embodiment of FIG. 14, an external magnet 1436 may be placed adjacent to the recipient's tissue 219 that covers the treatment substance reservoir 1402. The poles of the external magnet 536 and the magnetic element 1434 may be oriented so that the external magnet and the magnetic element will be magnetically attracted to one another when in proximity to one another. The mutual attraction between the external magnet 1436 and the magnetic element 1434 compresses the recipient's tissue 219 adjacent to the treatment substance reservoir 1402. The compression of the tissue, in turn, compresses the reservoir 1402. The positioning of the reservoir 1402 abutting the magnetic element 1434 and the superior portion 118 of the mastoid 115 provides a rigid surface that counters the compression of the tissue 219. As a result, a pressure change occurs in the treatment substance reservoir 1402 so as to force a portion of the treatment substance out of the reservoir through valve 1458. Once the magnet 1436 is removed, the flow of treatment substance from the reservoir 1402 terminates.

The valve 1458 may be a check valve or a stop-check valve (e.g., a magnetically operated valve). In embodiments in which the valve 1458 is a magnetically operated valve, the external magnet 1436 may be configured so as to compress the treatment substance reservoir 1402 and additionally open valve 1458.

Additionally, the external magnet 1436 may be placed adjacent to the recipient's tissue 219 that covers the flushing reservoir 1452 so as to activate the flushing module 1475. More specifically, the poles of the external magnet 1436 and the magnetic element 1444 may be oriented so that the external magnet and the magnetic element will be magnetically attracted to one another when in proximity to one another. The mutual attraction between the external magnet 1436 and the magnetic element 1444 compresses the recipient's tissue 219 adjacent to the flushing reservoir 1452. The compression of the tissue, in turn, compresses the reservoir 1452. The positioning of the reservoir 1452 abutting the magnetic element 1444 and the superior portion 118 of the mastoid 115 provides a rigid surface that counters the compression of the tissue 219. As a result, a pressure change occurs in the flushing reservoir 1452 so as to force a portion of the flushing solution out of the reservoir through valve 1468. Once the magnet 1436 is removed, the flow of flushing solution from the reservoir 1452 terminates.

The valve 1468 may be a check valve or a stop-check valve (e.g., a magnetically operated valve). In embodiments in which the valve 1468 is a magnetically operated valve, the external magnet 1436 may be configured so as to compress the reservoir 1452 and additionally open valve 1452.

The activation of the flushing module 1475 to release the flushing solution may occur after delivery of a treatment substance. The flushing solution is designed to clean the downstream portions of the delivery system, including the delivery tube 1406 and the delivery device 1408. That is, the flushing solution substantially removes any remaining treatment substance from the system so that the treatment substance does not precipitate and accrete within the system.

In the embodiment of FIG. 14, the same external magnet 1436 is used to activate both the treatment substance delivery and the flushing mechanisms. In certain arrangements, the flushing reservoir 1452 is implanted a certain distance away from the reservoir 1402 such that activation of the treatment substance delivery mechanism does not affect the flushing module 1475, and vice versa. However, in another arrangement shown in FIG. 14, the treatment substance delivery and the flushing mechanisms are responsive to different poles of the magnet 1436.

A magnet, such as magnet 1436, is an object that produces a magnetic field that interacts with other magnetic fields. Magnets have two poles, typically referred to as the "north pole" and the "south pole." The magnetic field may be represented by field lines that start at a magnet's north pole and end at the magnet's south pole. The magnetic force (attraction) between to magnetic objects is caused by the magnet's magnetic field and points in the direction of the field lines. For example, if two magnets are next to each other and their north poles are facing towards one another (or conversely if their south poles are facing towards one another), the field lines move away from each other and thus the magnets repel one another. In contrast, if two magnets are next to each other and a north pole of one magnet faces the south pole of the other magnet, the magnets will be attracted to one another.

The embodiment of FIG. 14 makes use of the opposing poles of the magnets to ensure that only one of the treatment substance delivery or the flushing mechanism is activated at any one time. More specifically, the magnetic element 1434 may be implanted such that either the north or the south pole of the magnetic element 1434 faces the tissue of the 219 of the recipient. The magnetic element 1444 is implanted such that the opposing pole faces the tissue 219 of the recipient (i.e., if the magnetic element 1434 has a north pole facing the tissue, the magnetic element 144 has a south pole facing the tissue). Similarly, in embodiments using magnetic valves, the valves 1458 and 1468 may be similarly responsive to different magnet poles.

The opposing surfaces 1437(1) and 1437(2) of the external magnet may be selected positioned adjacent the recipient's tissue 219 to activate either the treatment substance delivery or the flushing mechanisms. The opposing surfaces 1437(1) and 1437(2) may also be labeled so that user can easily identify how the external magnet 1436 should be placed to activate each mechanism.

In an alternative embodiment of FIG. 14, the flushing reservoir 1452 could also or alternatively be coupled to the treatment substance reservoir 1402 so as to flush both the treatment substance reservoir 1402 and the delivery tube 1406. Alternatively, a double valve or other mechanism may be present to enable selective and independent flushing of the treatment substance reservoir 1402 and the delivery tube 1406.

Accretion prevention (anti-accretion) mechanisms in accordance with embodiments presented herein may further include different shapes/configurations for the delivery device 1408 that prevent accretion. For example, the delivery device 1408 may include grooves, a sharp bevel, and/or a sponge/del device that is held below a groove in the tube to absorb any treatment substance that might be residually in the delivery tube 1406.

FIG. 15 is a cross-sectional view of part of another delivery system 1500 configured to prevent accretion resulting from treatment substance precipitation. In this embodiment, the delivery system 1500 is similar to the arrangements of FIGS. 8A-8C or FIG. 9, but further includes a replaceable delivery tube 1506 that passes through the recipient's tympanic membrane 104.

More specifically, a replaceable delivery tube 1506 has a proximal end that is fluidically coupled to a valve or reservoir and a distal end 1514 that is fluidically coupled to the round window 121. A delivery device 1508 is positioned in the distal end 1514 adjacent to the round window 121. Additionally, an elongate fixed sheath 1590 is extends from the valve or reservoir and to distal end 1594 that is attached to the round window 121 and/or another area of the recipient.

The delivery tube 1506 and the outer fixed sheath 1590 extend through the recipient's tympanic membrane 104 to the round window 121. In particular, the delivery tube 1506 and the outer fixed sheath 1590 pass through a surgically formed opening within the tympanic membrane 104. A surgically placed grommet 1556 is disposed around the fixed sheath 1590 so as to seal the opening in the tympanic membrane 104 around the fixed sheath 1590.

As shown, the fixed sheath 1590, and not the delivery tube 1506, is affixed to the tympanic membrane 104 (via the grommet 1556) and the recipient's inner ear 107. Additionally, the delivery tube 1506 is slideably engaged with the fixed sheath 1590. As a result, the delivery tube 1506 may be removed from the recipient's ear canal without damaging the tympanic membrane 104 or the inner ear 107. A replacement delivery tube 1506 may then be inserted. Periodic replacement of the delivery tube 1506 (and the delivery device 1508 therein) prevents accretion of precipitated treatment substance particles.

Embodiments have been primarily described above with reference to the coupling of the distal end of the delivery tube to a recipient's inner ear (e.g., round window) for delivery of the treatment substances to the cochlea. It is to be appreciated that treatment substances may be delivered to other regions of the recipient's ear. For example, the distal end of the delivery tube can be attached to or formed as a pouch or a sheet to envelope or cover a component of another device (e.g., a cochlear implant, direct acoustic stimulator, etc.) that has been infected or implanted in high risk location.

It is also to be appreciated that other locations and/or configurations for the various components disclosed herein are possible. For example, in one alternative arrangement a reservoir, valve, etc. may be positioned inside the recipient's cochlea.

Additionally, embodiments have been primarily described with reference to the use of a single reservoir for a treatment substance. It is to be appreciated that other embodiments may use two different reservoirs for different treatment substances. Alternatively, one reservoir may be subdivided in two sections for independent delivery of two different treatment substances. In one such embodiment, the two reservoirs or sub-reservoirs may be activated independently or a single push could activate both of the reservoirs or sub-reservoirs simultaneously.

It is to be appreciated that embodiments presented herein are not mutually exclusive and can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus, comprising:
    an implantable reservoir configured to have a treatment substance disposed therein;
    an implantable delivery tube having a proximal end fluidically coupled to the reservoir and a distal end positioned adjacent to an inner ear of a recipient of an implantable auditory prosthesis; and
    a passive activation mechanism configured to transfer a portion of the treatment substance in the reservoir to the delivery tube for delivery to the inner ear of the recipient,
    wherein the passive activation mechanism includes at least one resiliently flexible portion of the reservoir configured to deform in response to application of a user applied external force applied through the skin of the recipient so as to propel a portion of the treatment substance from the reservoir to the delivery tube.

2. The apparatus of claim 1, further comprising:
an implanted magnetic positioning member located adjacent the least one resiliently flexible portion of the reservoir configured to mate with a magnet of an external actuator.

3. The apparatus of claim 1, further comprising:
a secondary reservoir connected between the reservoir and the delivery tube.

4. The apparatus of claim 1, further comprising:
one or more fixation mechanisms configured to retain various components of the apparatus at a selected implanted location to ensure that the treatment substance is delivered to the inner ear.

5. The apparatus of claim 4, wherein at least one fixation mechanism comprises an elongate wire extending through a section of the delivery tube.

6. The apparatus of claim 4, wherein at least one fixation mechanism comprises an elongate wire mesh disposed around a section of the delivery tube.

7. The apparatus of claim 4, wherein at least one fixation mechanism comprises:
an implantable delivery tube positioning mechanism comprising a first extension arm configured to be secured to tissue of the recipient and a second extension arm configured to retain a portion of the delivery tube, wherein the first and second extension arms are connected by a joint that permits adjustment of the second extension arm relative to the first extension arm.

8. The apparatus of claim 1, further comprising a delivery device disposed at the distal end of the delivery tube configured to transfer the treatment substance from the delivery tube to the inner ear.

9. The apparatus of claim 1, further comprising:
a magnetically activated check valve fluidically coupling the reservoir to the implantable delivery tube, wherein the magnetically activated check valve is configured to open in response to an externally applied magnetic field.

10. A method, comprising:
implanting an implantable reservoir in a head of a recipient of an implantable auditory prosthesis, wherein the implantable reservoir is implanted adjacent to skin of the recipient and is configured to have a treatment substance disposed therein, and wherein the implantable reservoir includes at least one resiliently flexible portion configured to deform in response to application of a user applied external force applied through the skin of the recipient;
implanting an implantable delivery tube in the recipient so that a proximal end of the delivery tube is fluidically coupled to the reservoir and a distal end of the delivery tube is positioned adjacent an inner ear of a recipient; and
receiving, through the skin of the recipient, a user applied external force to cause the at least one resiliently flexible portion of the reservoir to deform and propel a portion of the treatment substance from the reservoir to the delivery tube for delivery to the inner ear.

11. The method of claim 10, wherein the implantable delivery tube comprises an elongate wire extending through a section of the delivery tube.

12. The method of claim 10, wherein the implantable reservoir is fluidically coupled to the delivery tube via a magnetically activated check valve, and wherein the method further comprises:
positioning an external magnet in a proximity to the magnetically activated check valve to open the magnetically activated check valve.

* * * * *